(12) United States Patent
Higashiyama et al.

(10) Patent No.: US 10,716,463 B2
(45) Date of Patent: Jul. 21, 2020

(54) ENDOSCOPE AND ENDOSCOPE SYSTEM

(71) Applicant: PANASONIC I-PRO SENSING SOLUTIONS CO., LTD., Fukuoka (JP)

(72) Inventors: Seiji Higashiyama, Fukuoka (JP); Yuuichi Takenaga, Fukuoka (JP); Haruyasu Katahira, Fukuoka (JP)

(73) Assignee: PANASONIC I-PRO SENSING SOLUTIONS CO., LTD., Fukuoka (JP)

(*) Notice: Subject to any disclaimer, the term of this patent is extended or adjusted under 35 U.S.C. 154(b) by 59 days.

(21) Appl. No.: 16/126,670

(22) Filed: Sep. 10, 2018

(65) Prior Publication Data

US 2019/0076007 A1 Mar. 14, 2019

(30) Foreign Application Priority Data

Sep. 11, 2017 (JP) .................. 2017-174388

(51) Int. Cl.
| | |
|---|---|
| *A61B 1/06* | (2006.01) |
| *H04N 9/04* | (2006.01) |
| *H04N 5/33* | (2006.01) |
| *G02B 27/12* | (2006.01) |

(Continued)

(52) U.S. Cl.
CPC ........ *A61B 1/0646* (2013.01); *A61B 1/00006* (2013.01); *A61B 1/00009* (2013.01);
(Continued)

(58) Field of Classification Search
CPC ............ A61B 1/00006; A61B 1/00009; A61B 1/00186; A61B 1/00195; A61B 1/04; A61B 1/042; A61B 1/043; A61B 1/0646; A61B 1/0684; G02B 23/2453; G02B 27/1013; G02B 27/126; G02B 27/141;
(Continued)

(56) References Cited

U.S. PATENT DOCUMENTS

| | | | | |
|---|---|---|---|---|
| 4,746,203 A | * | 5/1988 | Nishioka | A61B 1/05 348/E5.027 |
| 4,882,619 A | * | 11/1989 | Hasegawa | H04N 5/2253 348/337 |

(Continued)

FOREIGN PATENT DOCUMENTS

JP 2016-178995 A 10/2016

*Primary Examiner* — Peter D Le
(74) *Attorney, Agent, or Firm* — Greenblum & Bernstein P.L.C.

(57) ABSTRACT

An endoscope includes: an aperture portion having an opening to which light from an observation target site is incident; a filter unit that has a plurality of filters and selectively transmits light based on any one of the filters; a color separation prism that is formed by a plurality of separation prisms which separate light, which has transmitted through the filter unit, into beams of light having different color components from each other; a plurality of image sensors that are provided so as to respectively correspond to the separation prisms and capture an image based on the beams of light; a signal output unit that outputs image signals captured by the image sensors respectively; and a filter disposing unit that disposes any one of the plurality of filters so that the light is incident to the disposed one of the plurality of filters.

9 Claims, 20 Drawing Sheets

(51) Int. Cl.
*A61B 1/00* (2006.01)
*G02B 5/20* (2006.01)
*A61B 1/04* (2006.01)
*G02B 27/10* (2006.01)
*G02B 23/24* (2006.01)
*H04N 9/097* (2006.01)
*G02B 7/00* (2006.01)
*G02B 27/14* (2006.01)

(52) U.S. Cl.
CPC ...... *A61B 1/00186* (2013.01); *A61B 1/00195* (2013.01); *A61B 1/04* (2013.01); *A61B 1/042* (2013.01); *A61B 1/043* (2013.01); *A61B 1/0684* (2013.01); *G02B 5/208* (2013.01); *G02B 7/006* (2013.01); *G02B 23/2453* (2013.01); *G02B 27/1013* (2013.01); *G02B 27/126* (2013.01); *G02B 27/141* (2013.01); *G02B 27/145* (2013.01); *H04N 5/332* (2013.01); *H04N 9/0451* (2018.08); *H04N 9/097* (2013.01)

(58) Field of Classification Search
CPC ...... G02B 27/145; G02B 5/208; G02B 7/006; H04N 5/332; H04N 9/0451; H04N 9/097
See application file for complete search history.

(56) References Cited

U.S. PATENT DOCUMENTS

| | | | |
|---|---|---|---|
| 5,493,331 A * | 2/1996 | Takahashi | G07C 1/24 348/157 |
| 5,777,674 A * | 7/1998 | Ohmuro | G02B 27/1013 348/265 |
| 5,910,816 A * | 6/1999 | Fontenot | A61B 5/0059 348/162 |
| 10,122,975 B2 | 11/2018 | Hashimoto et al. | |
| 2002/0138008 A1* | 9/2002 | Tsujita | A61B 1/00009 600/473 |
| 2002/0177751 A1* | 11/2002 | Ueno | A61B 1/00009 600/160 |
| 2003/0043348 A1* | 3/2003 | Ito | G02B 27/1026 353/31 |
| 2003/0050532 A1* | 3/2003 | Doguchi | A61B 1/00186 600/109 |
| 2006/0241499 A1* | 10/2006 | Irion | A61B 1/00009 600/476 |
| 2009/0114820 A1* | 5/2009 | Murphy | G01J 3/02 250/339.01 |
| 2009/0234183 A1* | 9/2009 | Abe | A61B 1/00165 600/103 |
| 2009/0259098 A1* | 10/2009 | Krattiger | A61B 1/00096 600/109 |
| 2011/0187842 A1* | 8/2011 | Yamazaki | A61B 1/00057 348/68 |
| 2012/0268573 A1* | 10/2012 | Schonborn | A61B 1/051 348/49 |
| 2013/0060087 A1* | 3/2013 | Yoshida | A61B 1/00045 600/112 |
| 2014/0221752 A1* | 8/2014 | Miyano | A61B 1/04 600/162 |
| 2016/0286187 A1 | 9/2016 | Takenaga et al. | |
| 2016/0306180 A1* | 10/2016 | Rosa | G02B 27/1013 |

* cited by examiner

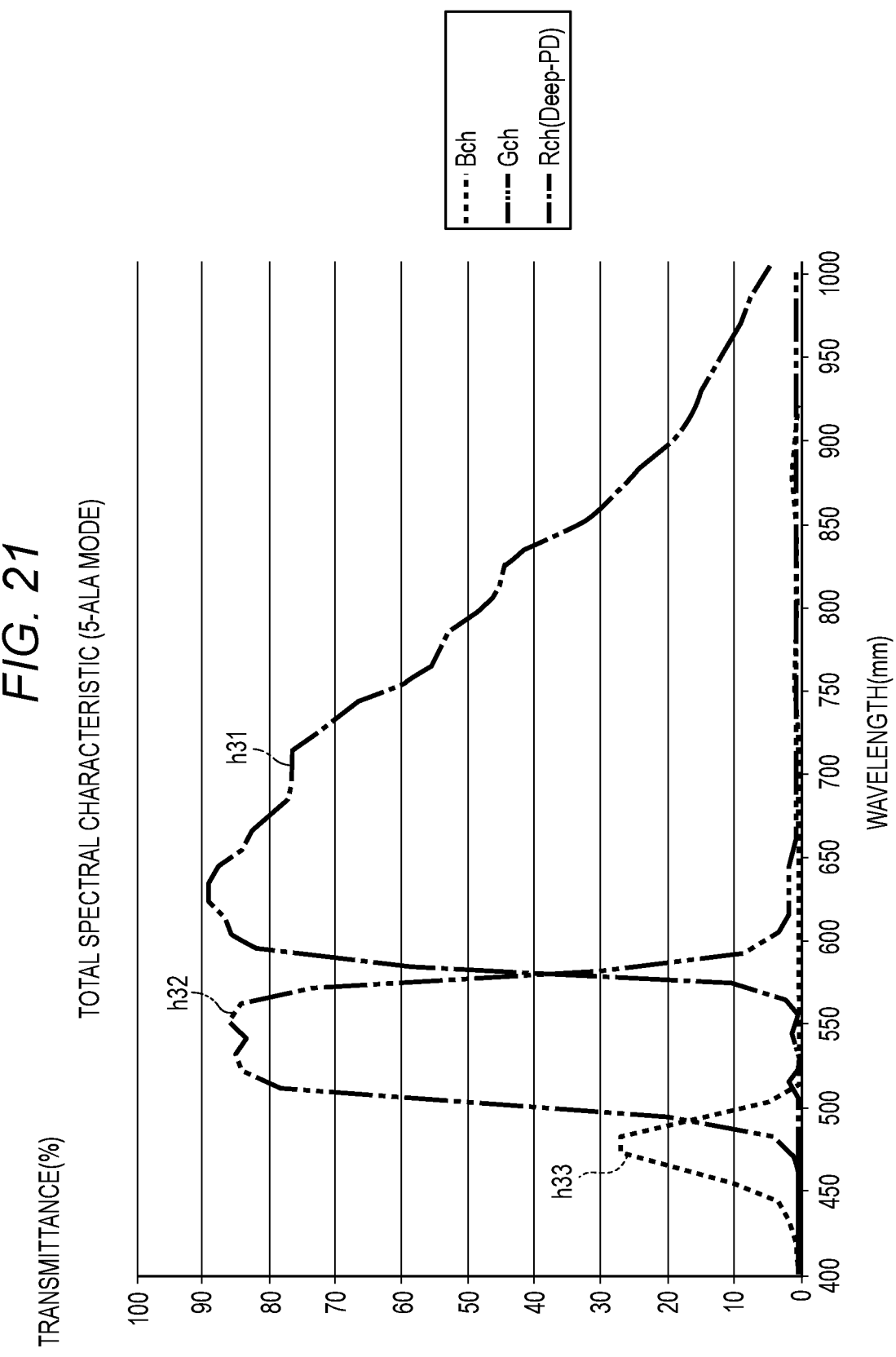

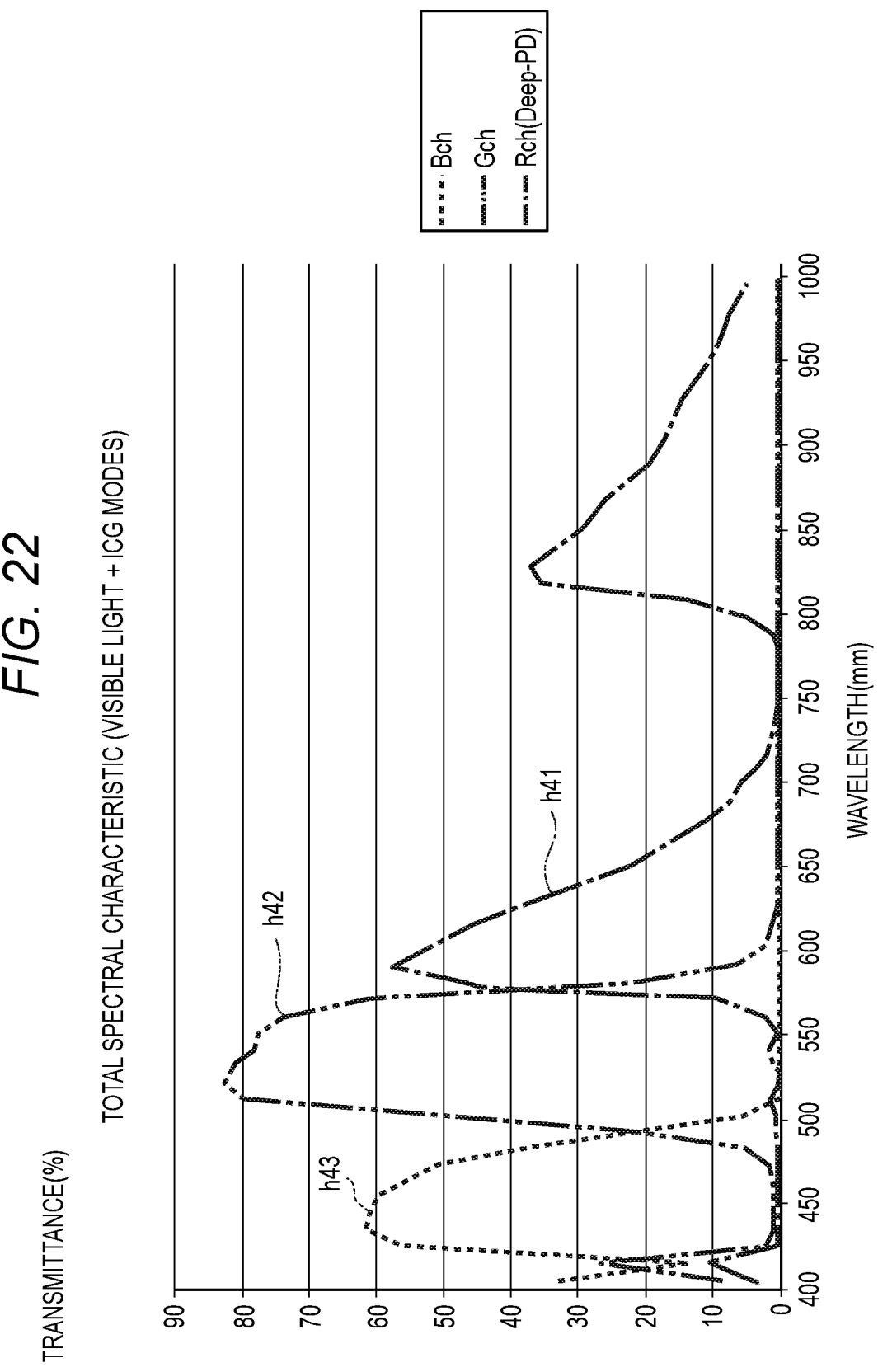

ENDOSCOPE AND ENDOSCOPE SYSTEM

BACKGROUND OF THE INVENTION

1. Field of the Invention

The present disclosure relates to an endoscope and an endoscope system.

2. Description of the Related Art

There has been known an endoscopic diagnosis of imaging a microlesion by a special light observation. Examples of the special light observation include a narrow-band light observation of performing a highlighting display of superficial blood vessels, a fluorescent observation of observing autofluorescence of a living body by irradiating a fluorescent substance (for example, a reagent or a dye) injected into a body with excitation light, an infrared light observation of extracting information of deep blood vessels by irradiation with infrared light having two different wavelengths, and the like. White light illumination is used in a normal observation by a doctor. By comparison, excitation light having a wavelength of 405 nm, for example, is used in the narrow-band light observation and the fluorescent observation, and infrared light having a wavelength of 760 nm, for example, is used in the infrared light observation. There has been proposed an endoscope that uses a four-plate prism so as to acquire imaging light having different wavelengths by an observation once and to process a plurality of items of information characterizing a lesion into an image useful for diagnosis. For example, the endoscope is disclosed in JP-A-2016-178995.

However, in the endoscopic diagnosis (for example, the fluorescent observation described above), unnecessary light such as excitation light, with which the fluorescent substance is irradiated, is imaged in a desired captured image with a target lesion as an object in some cases. In a technology of the related art, the captured image, in which such unnecessary light is imaged, is subjected to image quality adjustment by performing gain adjustment on an output of a signal having a target wavelength with low light intensity in an image processing device in a camera control unit (CCU) that is provided at a rear part from the endoscope. Therefore, when amplification is increased by the gain adjustment, an S/N ratio of the captured image decreases, and an image quality of the captured image deteriorates. Thus, it is not possible to suitably locate a lesion in some cases. In JP-A-2016-178995 described above, the fluorescent observation is mentioned; however, there is no consideration of a technical countermeasure against imaging of unnecessary light such as excitation light in a captured image.

SUMMARY OF THE INVENTION

The present disclosure is conceived in consideration of such circumstances in the related art described above, and an object thereof is to provide an endoscope and an endoscope system that suppress image quality deterioration of a captured image based on imaging of unnecessary light in an endoscopic diagnosis.

The present disclosure provides an endoscope including: an aperture portion having an opening to which light from an observation target site is incident, a filter unit that has a plurality of filters and selectively transmits light, which has passed through the opening, based on any one of the filters, a color separation prism that has a plurality of separation prisms which separate light, which has transmitted through the filter unit, into beams of light having different color components from each other, a plurality of image sensors that are provided so as to respectively correspond to the separation prisms and capture an image based on the beams of light having different color components separated by the separation prisms respectively, a signal output unit that outputs image signals captured by the image sensors respectively, and a filter disposing unit that disposes any one of the plurality of filters so that the light, which has passed through the opening, is incident to the disposed one of the plurality of filters.

In addition, the present disclosure provides an endoscope system including: an endoscope and a controller. The endoscope includes an aperture portion having an opening to which light from an observation target site is incident, a filter unit that has a plurality of filters and selectively transmits light, which has passed through the opening, based on any one of the filters, a color separation prism that is formed by a plurality of separation prisms which separate light, which has transmitted through the filter unit, into beams of light having different color components from each other, a plurality of image sensors that are provided so as to respectively correspond to the separation prisms and capture an image based on the beams of light having different color components separated by the separation prisms, a signal output unit that outputs image signals captured by the image sensors respectively, and a filter disposing unit that disposes any one of the plurality of filters so that the light, which has passed through the opening, is incident to the disposed one of the plurality of filters. The controller generates an RGB image and an IR image based on the image signals output from the signal output unit respectively and displays the RGB image and the IR image on a display unit.

According to the present disclosure, it is possible to efficiently suppress image quality deterioration of a captured image based on imaging of unnecessary light in the endoscopic diagnosis.

BRIEF DESCRIPTION OF DRAWINGS

FIG. 21 is a graph showing an example of a 5-ALA mode using the 5-ALA excitation-light cut filter.

FIG. 22 is a graph showing an example of a visible light and ICG mode using the ICG excitation-light cut filter.

DETAILED DESCRIPTION OF THE PREFERRED EMBODIMENTS

History to Content of Embodiment

In a surgery using an endoscope, indocyanine green (ICG) which is a fluorescent substance (such as a reagent or a dye) is administered, a site (that is, a target lesion) such as a tumor, to which the ICG is administered in the body, is irradiated with near-infrared light such that fluorescence emission is caused from the target lesion, and a site including the target lesion is imaged. When the near-infrared light (for example, a peak wavelength of 805 nm in a range of wavelength of 750 to 810 nm) causes excitation of the ICG, the ICG is a dye for causing fluorescence emission by near-infrared light having longer wavelength (for example, a peak wavelength of 835 nm).

In a case where a single-board camera that is configured with a single image sensor receives light including an IR component and acquires an image of a target lesion, four divided filters for a red (R) component, a green (G) component, a blue (B) component, and the IR component are provided on an incident surface (imaging surface) of the image sensor, for example. Therefore, in order to obtain desired color reproducibility and resolution, the image sensor needs to increase in size. Thus, it is difficult to apply the single-board camera to an endoscope.

Figure 19:
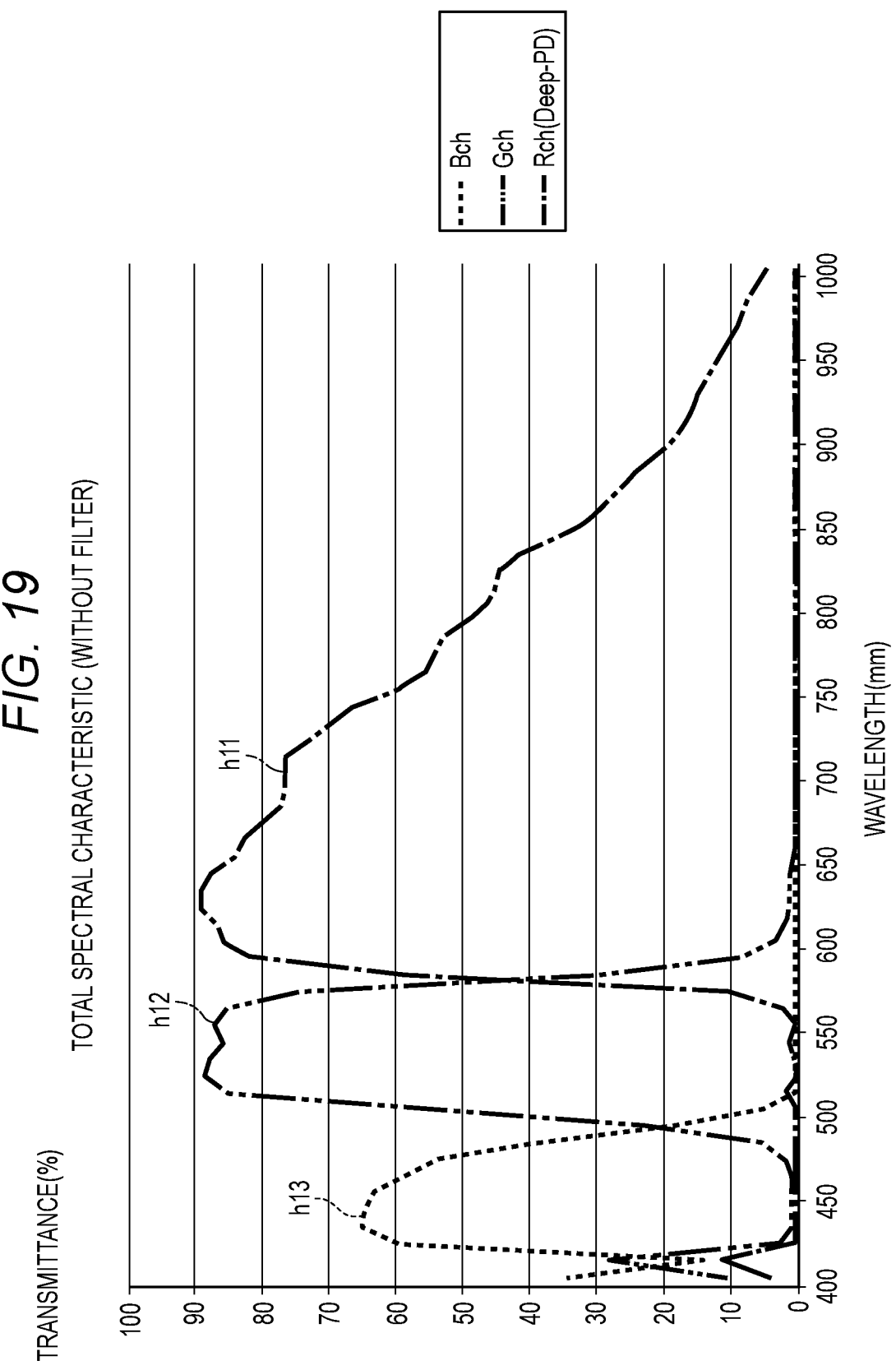
FIG. 19 is a graph showing an example of a total spectral characteristic of the four-color separation prism without using the filter.

In addition, in a case where a four-board camera uses a four-color separation prism that is formed by four color separation prisms and four image sensors provided to correspond to the four color separation prisms, and the four-board camera receives light including the IR component and acquires an image of the target lesion, a low signal strength of the IR component (for example, light having a wavelength of 800 nm or longer) is obtained, as shown in FIG. 19.

FIG. 19 is a graph showing an example of a total spectral characteristic of the four-color separation prism without using the filter. In FIG. 19, the vertical axis represents transmittance of each color, and the horizontal axis represents a wavelength. The transmittance corresponds to a ratio of a quantity of incident light to each of the prisms for the R component, the G component, and the B component and a quantity of incident light to the image sensors corresponding to the respective prisms. h11 represents transmittance of light having the R component. h12 represents transmittance of light having the G component. h13 represents transmittance of light having the B component. h11 also includes transmittance of light having the IR component.

In an endoscopic diagnosis (for example, a fluorescent observation), unnecessary light such as excitation light, with which the fluorescent substance is irradiated, is imaged in a desired captured image with a target lesion as an object in some cases. In a technology of the related art, the captured image, in which such unnecessary light is imaged, is subjected to image quality adjustment by performing gain adjustment on an output of a signal having a target wavelength with low light intensity in an image processing device in a CCU that is provided at a rear part from the endoscope. Therefore, when high amplification is performed by the gain adjustment, an S/N ratio of the captured image decreases, and an image quality of the captured image deteriorates. Thus, it is not possible to suitably locate a lesion in some cases. In JP-A-2016-178995 described above, the fluorescent observation is mentioned; however, there is no consideration of a technical countermeasure against imaging of unnecessary light such as excitation light in a captured image. In addition, as shown in FIG. 19, there is also a certain amount of transmittance of the excitation light (for example, 750 to 810 nm) of the ICG described above. Therefore, when imaging is performed based on the excitation light incident to the image sensor, unnecessary light such as the excitation light is reflected in the captured image, and detailed image information of an original observation target site such as a core target lesion.

In the following embodiments, in an endoscopic diagnosis, examples of an endoscope and an endoscope system that suppress image quality deterioration of a captured image based on imaging of unnecessary light are described.

Hereinafter, with reference to appropriate figures, embodiments (hereinafter, referred to as "the embodiments") that specifically disclose the endoscope and the endoscope system according to the present disclosure will be described in detail. However, the detailed description that is more than necessary is omitted in some cases. For example, the detailed description of a well-known subject or repetitive description of substantially the same configuration is omitted in some cases. This is because the following description avoids being unnecessarily redundant and is easy to be understood by those skilled in the art. The accompanying figures and the following description are provided to make those skilled in the art sufficiently understand the present disclosure and are not provided to limit subjects according to what is claimed. The endoscope according to the following embodiments is used for observing an observation target site in a body such as in the abdominal cavity (in other words, a target lesion in a body of a human).

[Configuration of Endoscope]

Figure 1:
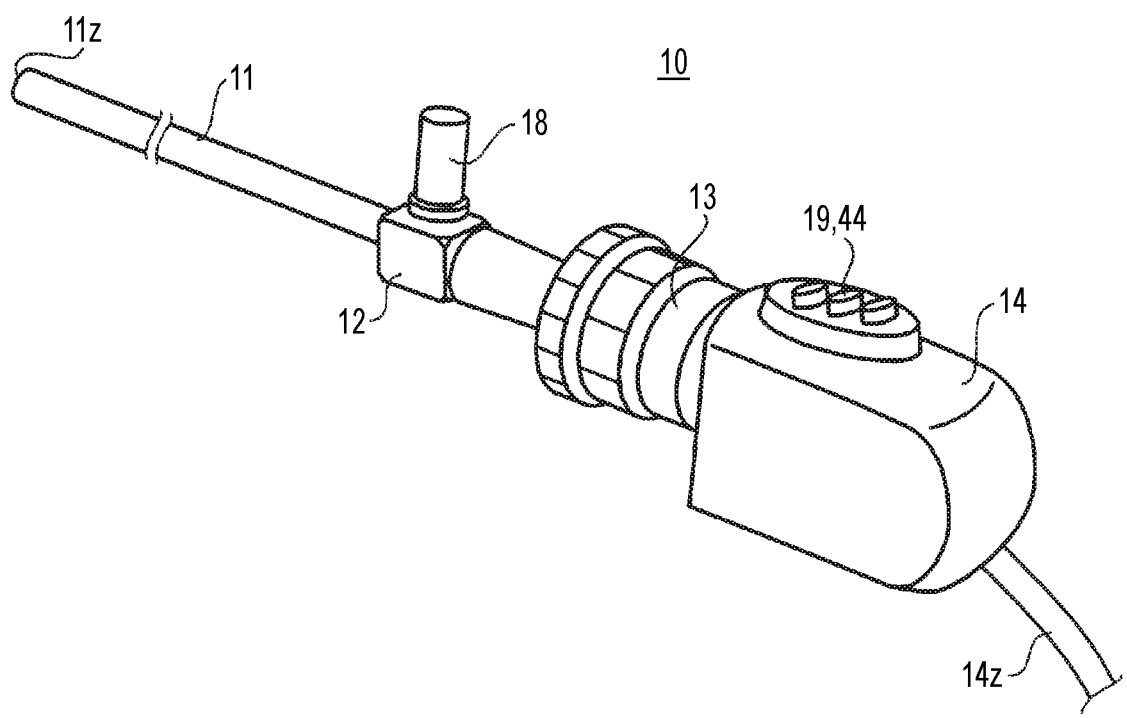
FIG. 1 is a view showing the external appearance of an example of an endoscope according to an embodiment.
Figure 2:
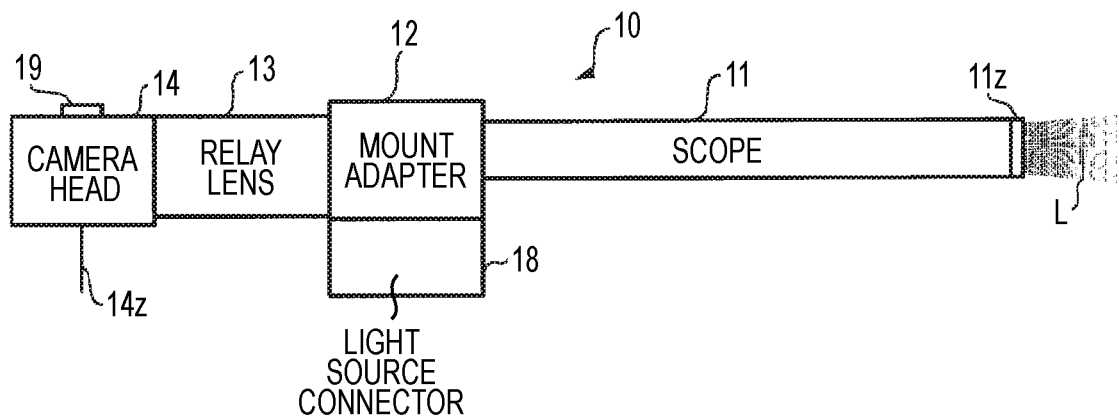
FIG. 2 is a schematic diagram showing an example of an outline configuration of the endoscope according to the embodiment.

FIG. 1 is a view showing the external appearance of an example of an endoscope 10 according to the embodiment. FIG. 2 is a schematic diagram showing an example of an outline configuration of the endoscope 10 according to the embodiment. The endoscope 10 is a medical apparatus that can be handled with one hand by a user, for example. The endoscope 10 is configured to include a scope 11, a mount adapter 12, a relay lens 13, a camera head 14, operation switches 19 and 44, and a light source connector 18.

The scope 11 is inserted into a body of a human (observed person), is a main part of a rigid endoscope, for example, and is an elongated light guiding member that is capable of guiding light from a proximal end to a distal end. The scope 11 has an imaging window 11z at the distal end, an optical fiber that transfers light of an observation target site (for example, a target lesion), which is incident from the imaging window 11z, and an optical fiber that guides, to the distal end, light L guided from the light source connector 18. For example, the imaging window 11z is made of an optical material such as optical glass or optical plastic.

The mount adapter 12 is a member for attaching the scope 11 to the camera head 14. Various types of scopes can be detachably mounted on the mount adapter 12. In addition, the light source connector 18 is mounted on the mount adapter 12.

The light source connector 18 guides illumination light for illuminating a site (for example, a target lesion) in a human body from a light source device (not shown). The illumination light includes visible light and IR light. Light guided by the light source connector 18 is guided to the distal end of the scope 11 through the scope 11, and the site (target lesion) in the human body is irradiated with the light from the imaging window 11z. A light source is an LED light source, for example. The light source may be a light source such as a xenon lamp or a halogen lamp, instead of the LED light source.

The relay lens 13 forms an image (causes convergence of) light that is transmitted through the scope 11 on an imaging surface in the camera head 14. The relay lens 13 has a plurality of lenses and moves the lenses such that a focus is adjusted and a zoom magnification is adjusted depending on an amount of an operation of the operation switch 19.

Figure 13:
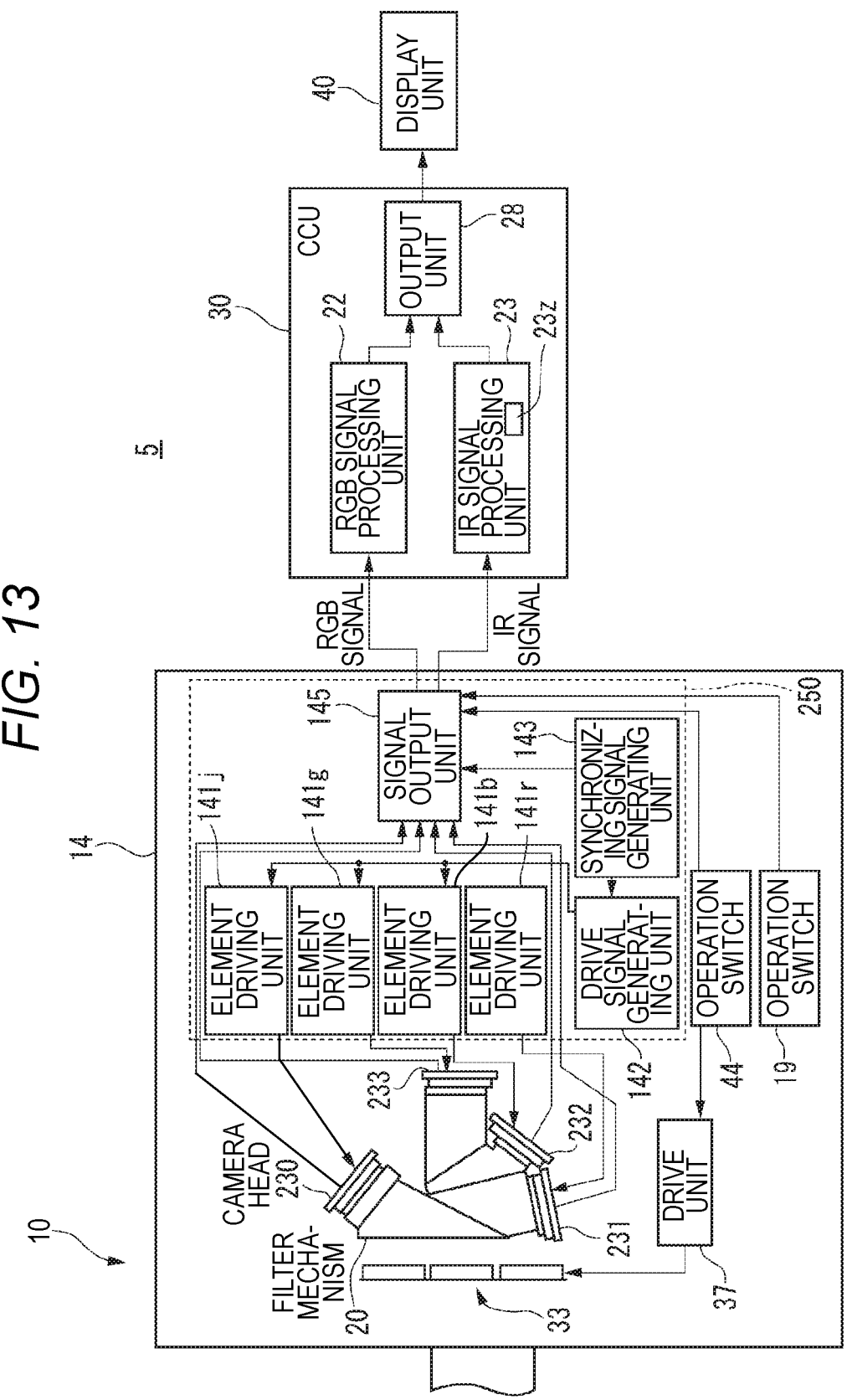
FIG. 13 is a block diagram showing an example of a configuration of an endoscope system according to the embodiment.

For example, the camera head 14 includes a housing that can be held by a hand of a user, a four-color separation prism 20 (refer to FIG. 5) that is a color separation prism, four image sensors 230, 231, 232, and 233 (refer to FIG. 5), and an electronic substrate 250 (refer to FIG. 13).

The four-color separation prism 20 is a four-board prism that separates the light converging on the relay lens 13 into three primary color light of R light (R component), G light (G component), and B light (B component) and IR light (IR component). The image sensors 230 to 233 convert optical images formed on the respective imaging surfaces thereof through the separation by the four-color separation prism 20 into image signals (electric signals).

An image sensor such as a charge coupled device (CCD) or a complementary metal oxide semiconductor (CMOS) is used for the image sensors 230 to 233.

The four image sensors 230 to 233 are dedicated sensors that receive beams of light having the IR component, the B component, the R component, and the G component, respectively. Therefore, unlike a single-board camera that receives beams of light having the IR component, the B component, the R component, and the G component by a single image sensor, it is possible to employ image sensors having a small size as the individual image sensors. For example, an image sensor having a size of ⅓ type (4.8 mm×3.6 mm) is used. In a case of the single-board camera, the image sensor needs to have a size of at least ⅔ type (8.8 mm×6.6 mm).

For example, in the electronic substrate 250 (refer to FIG. 13), a circuit including a signal output circuit that outputs a signal in a low volt digital signal (LVDS) method and a circuit (TG circuit) of timing generator (TG) is installed.

The signal output circuit that is installed in the electronic substrate 250 outputs, as a pulse signal, an RGB signal and an IR signal of images captured by the image sensors 230 to 233 by the low voltage digital signal (LVDS) method. The TG circuit that is installed in the electronic substrate 250 supplies a timing signal (synchronizing signal) to each unit in the camera head 14. The RGB signal is a signal containing at least one of the R component, the G component, and the B component.

In the camera head 14, a signal cable 14z for transferring an image signal to a camera control unit (CCU) 30 to be described below is mounted.

Figure 3:
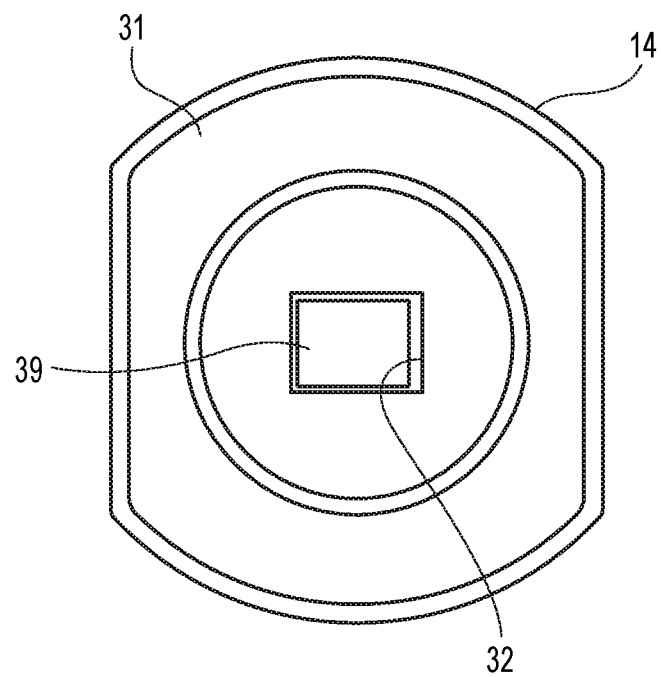
FIG. 3 is a front view of a camera head.

FIG. 3 is a front view of the camera head 14. An aperture member 31 is attached to a connection opening of the relay lens 13 on an objective side of the camera head 14. A rectangular opening 32 is formed at the central portion of the aperture member 31. The opening 32 causes the light from the observation target site (for example, the target lesion) to be incident to an IR separation prism (refer to the description below) provided on the most objective side of the four-color separation prism 20. The opening 32 functions as a so-called and aperture stop. The aperture stop limits light beam fluxes which converge on the relay lens 13. Filters of a filter unit 33 (refer to FIG. 4) are selectively disposed on an opposite side to the objective side with the opening 32 interposed therebetween.

Figure 4:
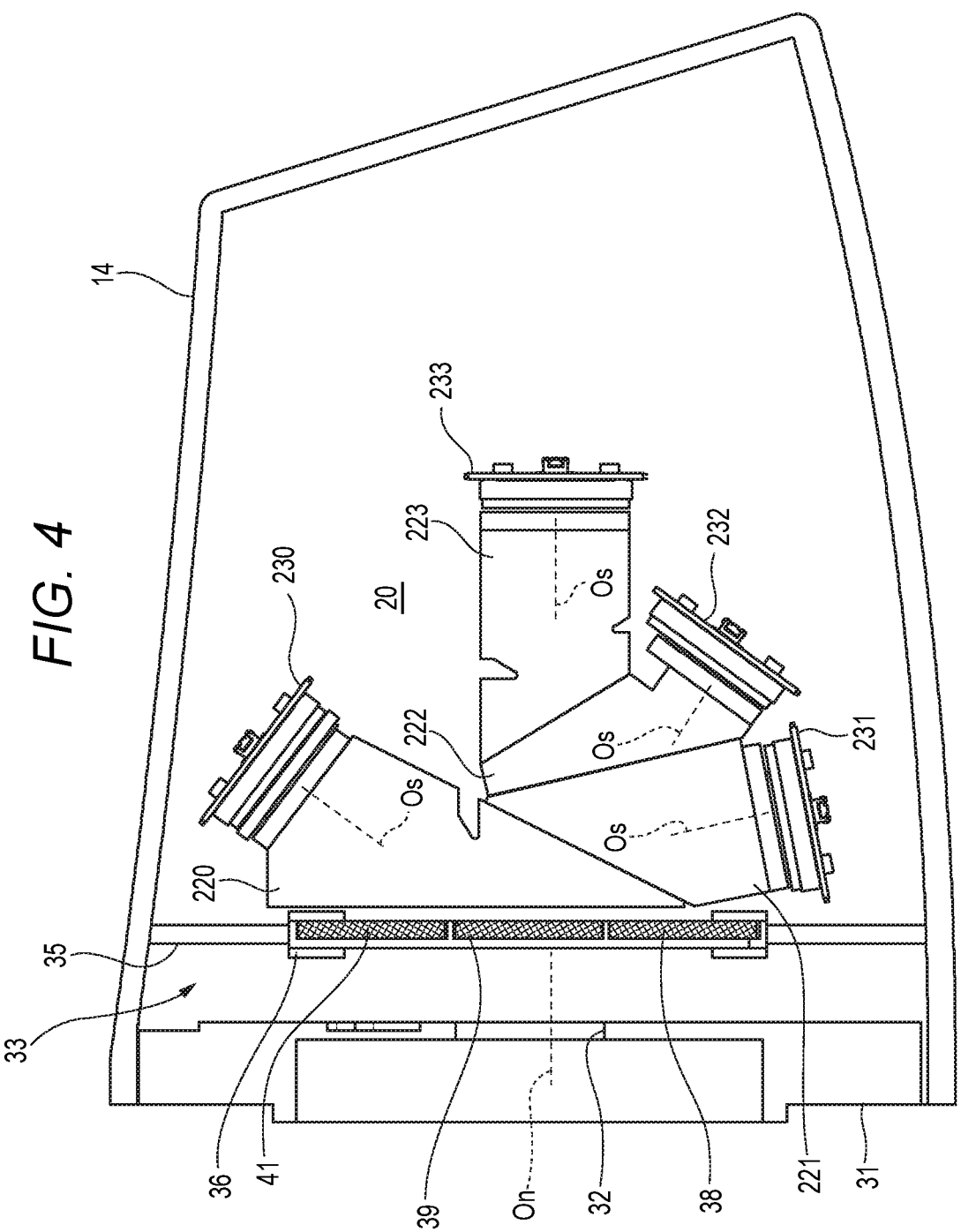
FIG. 4 is a side view of an inside of the camera head in which a four-color separation prism and a filter unit are provided.

FIG. 4 is a side view of an inside of the camera head in which the four-color separation prism and the filter unit are provided. In the camera head 14, the four-color separation prism 20 is disposed on a side of the aperture member 31 which is opposite to the objective side. The filter unit 33 is disposed between the four-color separation prism 20 and the aperture member 31.

Figure 5:
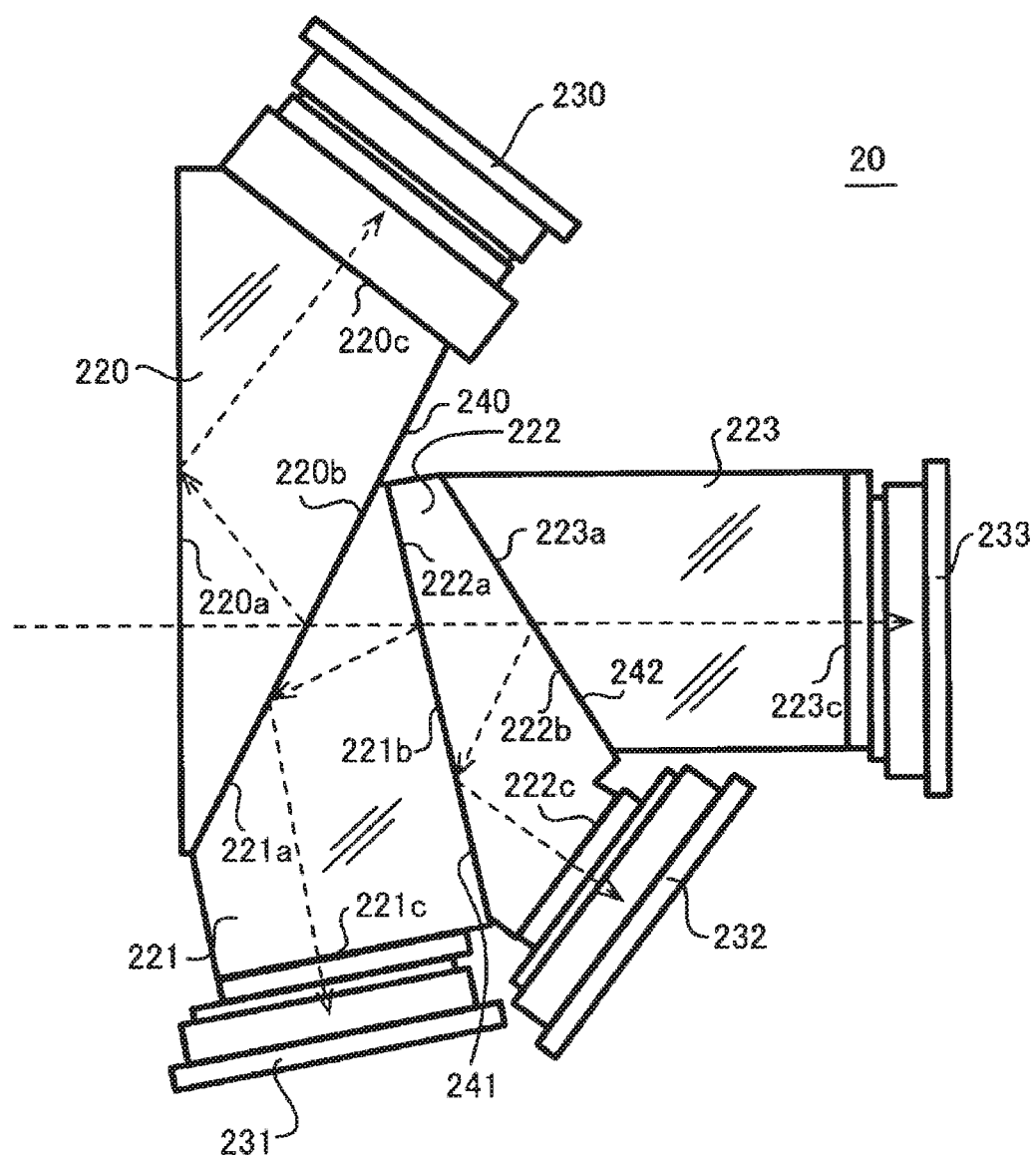
FIG. 5 is a schematic view showing an example of a structure of the four-color separation prism.

FIG. 5 is a schematic view showing an example of a structure of the four-color separation prism 20. The four-color separation prism 20 (an example of a color separation prism) separates the light (that is, incident light) from the observation target site (for example, the target lesion), which is guided by the relay lens 13, into three primary light having the R component, the G component, and the B component and the light having the IR component. In the four-color separation prism 20, an IR separation prism 220, a blue separation prism 221, a red separation prism 222, and a green separation prism 223 which are four separation prisms are assembled in this order in an optical axis direction.

The image sensor 230 for IR is disposed to be opposite to an emission surface 220c of the IR separation prism 220.

The image sensor 231 for blue is disposed to be opposite to an emission surface 221c of the blue separation prism 221.

The image sensor 232 for red is disposed to be opposite to an emission surface 222c of the red separation prism 222.

The image sensor 233 for green is disposed to be opposite to an emission surface 223c of the green separation prism 223.

The image sensors 230 to 233 are CCD or CMOS image sensors including pixels arranged in a horizontal (H) direction and a vertical (V) direction, for example. The image sensors 230 to 233 convert optical images formed on the respective imaging surfaces from the light obtained by the separation of the colors of IR, R, G, and B into electric signals. In other words, the image sensors 230 to 233 are provided to correspond to the respective separation prisms and perform imaging based on the light having different color components separated by the respective separation prisms.

In the IR separation prism 220, incident light is incident to an incident surface 220a of the IR separation prism 220. Light reflected from a reflective surface 220b that is opposite to the incident surface 220a is totally reflected on a boundary of the incident surface 220a of the IR separation prism 220, is emitted from the emission surface 220c that is opposite to the incident surface 220a, and is incident to the image sensor 230 for IR. For example, an IR reflective film 240 is formed on the reflective surface 220b by vapor deposition. The IR separation prism 220 reflects light having the IR component of the incident light and transmits the other light (light having the B component, the R component, and the G component). The image sensor 230 for IR causes light reflected from the reflective surface 220b and the incident surface 220a total twice to be incident thereto and receives light. The IR separation prism 220 is molded such that light travels in such a manner in the IR separation prism 220.

In the blue separation prism 221, light (incident light) transmitted through the IR separation prism 220 is incident to an incident surface 221a of the blue separation prism 221. Light reflected from a reflective surface 221b that is opposite to the incident surface 221a is totally reflected on a boundary of the incident surface 221a of the blue separation prism 221, is emitted from the emission surface 221c that is opposite to the incident surface 221a, and is incident to the image sensor 231 for blue. For example, a blue reflective film 241 is formed on the reflective surface 221b by vapor deposition. The blue separation prism 221 reflects light having the B component of the incident light and transmits the other light (light having the R component and the G component). The image sensor 231 for blue causes light reflected from the reflective surface 221b and the incident surface 221a total twice to be incident thereto and receives light. The blue separation prism 221 is molded such that light travels in such a manner in the blue separation prism 221.

In the red separation prism 222, light (incident light) transmitted through the blue separation prism 221 is incident to an incident surface 222a of the red separation prism 222. Light reflected from a reflective surface 222b that is opposite to the incident surface 222a is totally reflected on a boundary of the incident surface 222a of the red separation prism 222, is emitted from the emission surface 222c that is opposite to the incident surface 222a, and is incident to the image sensor 232 for red. For example, a red reflective film 242 is formed on the reflective surface 222b by vapor deposition. The red separation prism 222 reflects light having the R component of the incident light and transmits the other light (light having the G component). The image sensor 232 for red causes light reflected from the reflective surface 222b and the incident surface 222a total twice to be incident thereto and receives light. The red separation prism 222 is molded such that light travels in such a manner in the red separation prism 222.

In the green separation prism 223, light (incident light) transmitted through the red separation prism 222 is incident to an incident surface 223a of the green separation prism 223, is emitted from the emission surface 223c that is opposite to the incident surface 223a, and is incident to the image sensor 233 for green. The green separation prism 223 is molded such that light travels in such a manner in the green separation prism 223.

Here, the image sensor 230 for IR may output the electric signal having pixel values (signal levels) as is; however, the image sensor may perform an adding process of H/V pixel values, in which pixel values of pixels adjacent in the horizontal (H) and vertical (V) directions are added, and may output an electric signal having a pixel value obtained after the adding process of the H/V pixel values.

For example, when the H/V pixel values are subjected to the adding process, and a pixel value of the image sensor 230 for IR is about "30", a pixel value of the IR component is "120" (=30×4) by performing pixel addition.

Provided that a pixel value of an IR component is about "10" in the related art. According to the endoscope 10 of the embodiment, the image sensor 230 for IR is independently provided, and thereby the pixel value of the IR component is obtained to be 3 times to 12 times the pixel value of the related art.

In addition, provided that the pixel values of the image sensors 231 to 233 for RGB of the embodiment are about "100". In this case, when the adding process of the H/V pixel values are performed, signal levels of the R component, the G component, and the B component are substantially the same level as the signal level of the IR component, and thus it is easy to view an RGB image and an IR image. The RGB image is an image obtained from at least one signal of the R component, the G component, and the B component. The IR image is an image obtained from the signal of the IR component.

Figure 6:
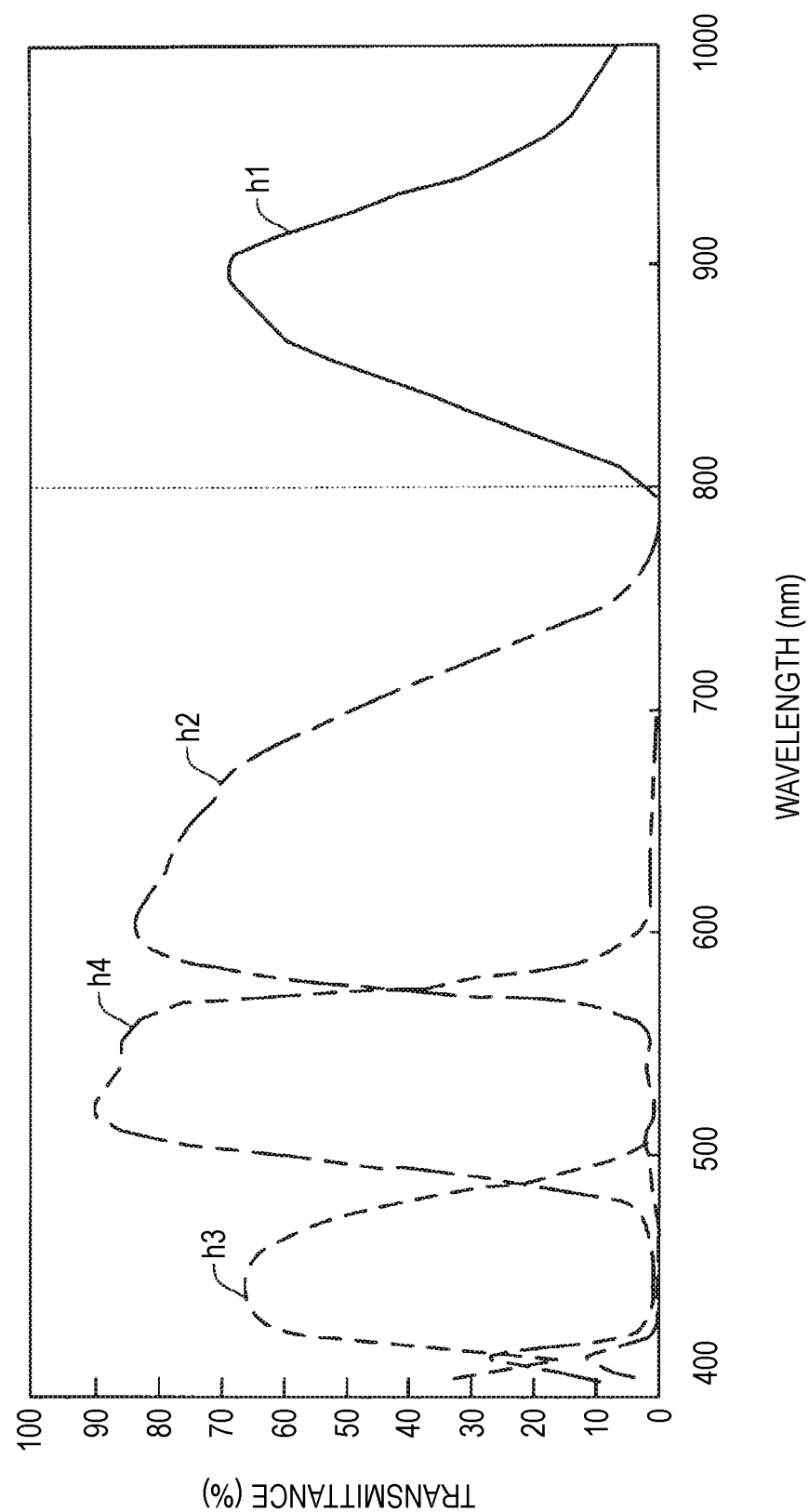
FIG. 6 is a graph showing an example of a spectral characteristic of the four-color separation prism.

FIG. 6 is a graph showing an example of a spectral characteristic of the four-color separation prism 20. The vertical axis in FIG. 6 represents the transmittances (%) and corresponds to a ratio of a quantity of incident light to the image sensors 230 to 233 corresponding to the respective prisms to a quantity of the incident light to the prisms. The horizontal axis in FIG. 6 represents a wavelength (nm) of light that is incident to the image sensors 230 to 233.

In FIG. 6, a waveform h1 (solid line) represents a spectral characteristic of light having the IR component, which is incident to the image sensor 230 for IR. Of the light incident to the four-color separation prism 20, the transmittance of the light having the IR component, which is incident to the image sensor 230 for IR, has a peak waveform having about 70% of transmittance at an approximate wavelength of 900 nm in a range of wavelength of 800 to 1,000 nm.

A waveform h2 (dot-and-dash line) represents a spectral characteristic of the light having the R component, which is incident to the image sensor 232 for red. The transmittance of the light having the R component, which is incident to the image sensor 232 for red, has a peak waveform having about 80% of transmittance at an approximate wavelength of 600 nm.

A waveform h3 (dotted line) represents a spectral characteristic of the light having the B component, which is incident to the image sensor 231 for blue. The transmittance of the light having the B component, which is incident to the image sensor 231 for blue, has a peak waveform having higher than 60% of transmittance at an approximate wavelength of 450 nm.

A waveform h4 (two-dot chain line) represents a spectral characteristic of the light having the G component, which is incident to the image sensor 233 for green. The transmittance of the light having the G component, which is incident to the image sensor 233 for green, has a peak waveform having about 90% of transmittance at an approximate wavelength of 530 nm.

As described above, the transmittances of the light having the IR component, the R component, the B component, and the G component separated by the four-color separation prism 20 are all higher than 60%. Hence, pixel values of the IR component, the R component, the B component, and the G component are preferably obtained, and it is necessary to significantly increase the image having the IR component. Consequently, in a case where the target lesion is imaged, color reproducibility of the captured image containing the IR component improves.

Incidentally, in the endoscopic diagnosis (for example, the fluorescent observation), when unnecessary light such as excitation light, with which a fluorescent substance (for example, a dye such as ICG) is irradiated, is imaged in a desired captured image, it is necessary to specifically locate the target lesion, and it is necessary to amplify a signal output having a target wavelength component. In this manner, when amplification is increased, an S/N ratio is degraded, and an image quality of the captured image deteriorates.

In the endoscope 10 according to the embodiment, a filter unit 33 shown in FIG. 4, which cuts unnecessary light that is incident to the four-color separation prism 20, is provided between the aperture member 31 and the four-color separation prism 20.

Figure 7:
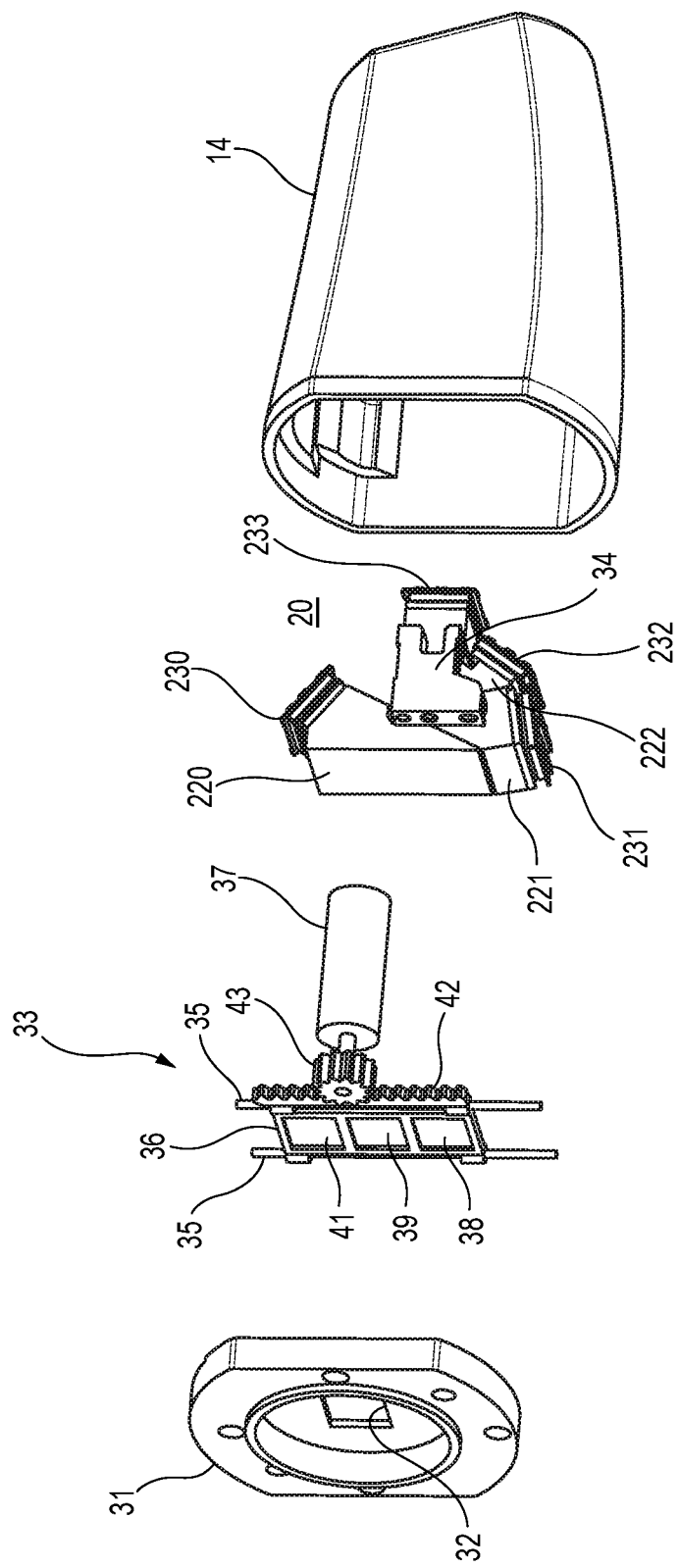
FIG. 7 is an exploded perspective view of main parts of the camera head.

FIG. 7 is an exploded perspective view of main parts of the camera head 14. The four-color separation prism 20 is fixed to a case of the camera head 14 by a support member 34. The support member 34 also supports the filter unit 33. In other words, the filter unit 33 is positioned to be relatively positioned with respect to the four-color separation prism 20 in the camera head 14 with high accuracy.

The filter unit 33 (an example of a filter unit) has a linear guide 35 that is supported by the support member 34, a filter holding frame 36 to which a plurality of optical wavelength filters to be described below are fixed, and a drive motor 37 (an example of a filter disposing unit). The linear guide 35 is configured with a pair of parallel rods. The linear guide 35 movably supports the filter holding frame 36 in a longitudinal direction of the pair of rods. The filter holding frame 36 is provided with a plurality of filter holding portions in a moving direction. In the embodiment, three filter holding portions are formed. The optical wavelength filters (an example of the filters) that selectively transmit or reflect the light that has passed through the opening 32 are fixed to the respective filter holding portions. In other words, the filter unit 33 causes the plurality of optical wavelength filters to slide substantially linearly with respect to the opening 32 in response to a predetermined user operation, for example, and is capable of selectively disposing any one of the plurality of optical wavelength filters.

As shown in FIG. 4, the four-color separation prism 20 is disposed such that the IR separation prism 220, the blue separation prism 221, the red separation prism 222, and the green separation prism 223 have a light flux center Os of the incident light thereof positioned along the same plane (the paper surface of FIG. 4). More preferably, the four-color separation prism 20 is disposed such that the IR separation prism 220, the blue separation prism 221, the red separation prism 222, and the green separation prism 223 have the light flux center Os of the incident light thereof positioned on the same plane. In addition, an IR cut filter 38, a 5-ALA excitation-light cut filter 39, and an ICG excitation-light cut filter 41 which are supported by the filter unit 33 are orthogonal to a light flux center On of the incident light to the IR separation prism 220 and linearly move to be parallel to the same plane described above.

In the embodiment, the optical wavelength filters (an example of the filter) constituting the filter unit 33 include the IR cut filter 38, the 5-ALA excitation-light cut filter 39, and the ICG excitation-light cut filter 41. The IR cut filter 38 has a spectral characteristic as the IR cut filter for causing normal light (for example, visible light) to pass therethrough and cutting IR light having a wavelength on a side on which the wavelength is longer than that of the normal light. The 5-ALA excitation-light cut filter 39 has a spectral characteristic as a 5-ALA excitation-light cut filter for cutting excitation light of 5-ALA (aminolevulinic acid) which is the fluorescent substance. The ICG excitation-light cut filter 41 has a spectral characteristic as an ICG excitation-light cut filter for cutting excitation light of ICG which is the fluorescent substance. In addition, the ICG excitation-light cut filter 41 may have not only the spectral characteristic as the ICG excitation-light cut filter but also the spectral characteristic as the IR cut filter described above, for example.

The IR cut filter 38 is used in a visible light mode (for example, a mode in which it is possible to image the visible light) and reflects (cuts) the light having the IR component. The 5-ALA excitation-light cut filter 39 is used in a 5-ALA mode (for example, a mode in which it is possible to cut the excitation light of 5-ALA and to perform the imaging) and cuts narrow-band 5-ALA excitation light including a wavelength of 400 nm. The ICG excitation-light cut filter 41 is used in ICG and visible light modes (for example, a mode in which it is possible to cut the excitation light of ICG and the IR light and to perform the imaging) and cuts narrow-band ICG excitation light and the IR light including a wavelength of 780 nm.

Figure 8:
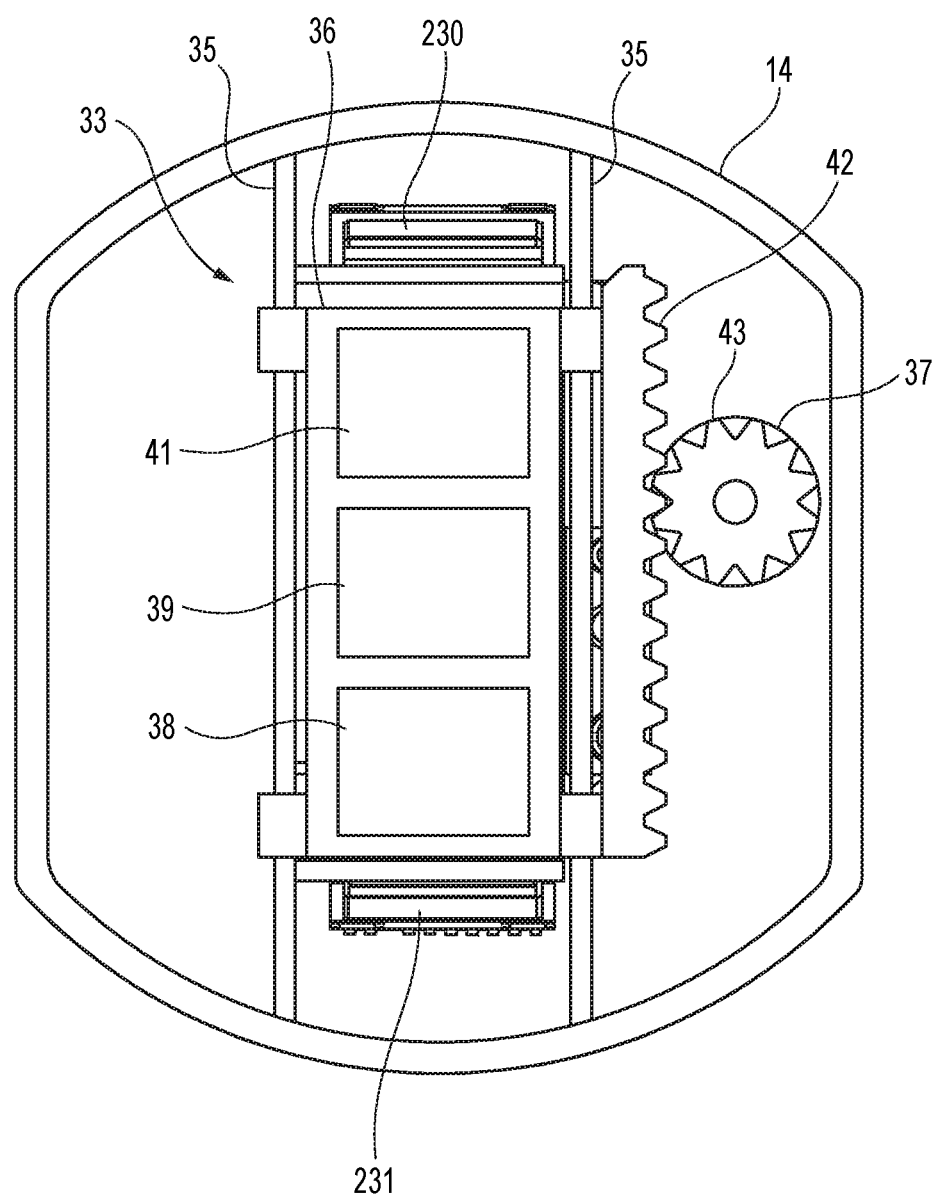
FIG. 8 is a front view of the filter unit.

FIG. 8 is a front view of the filter unit 33. In the filter unit 33, a rack 42 provided with a plurality of teeth in a moving direction is fixed to a side portion of the filter holding frame 36. A pinion 43 fixed to a drive axis of the drive motor 37 meshes with the rack 42. The drive motor 37 is instructed to perform driving by an operation (an example of the predetermined user operation) of the operation switch 44 that is provided on the camera head 14. The drive motor 37 (an example of the filter disposing unit) moves the rack 42 vis the pinion 43 substantially linearly (including linear movement), thereby selectively disposing any one of the IR cut filter 38, the 5-ALA excitation-light cut filter 39, and the ICG excitation-light cut filter 41 at the opening 32.

Figure 9:
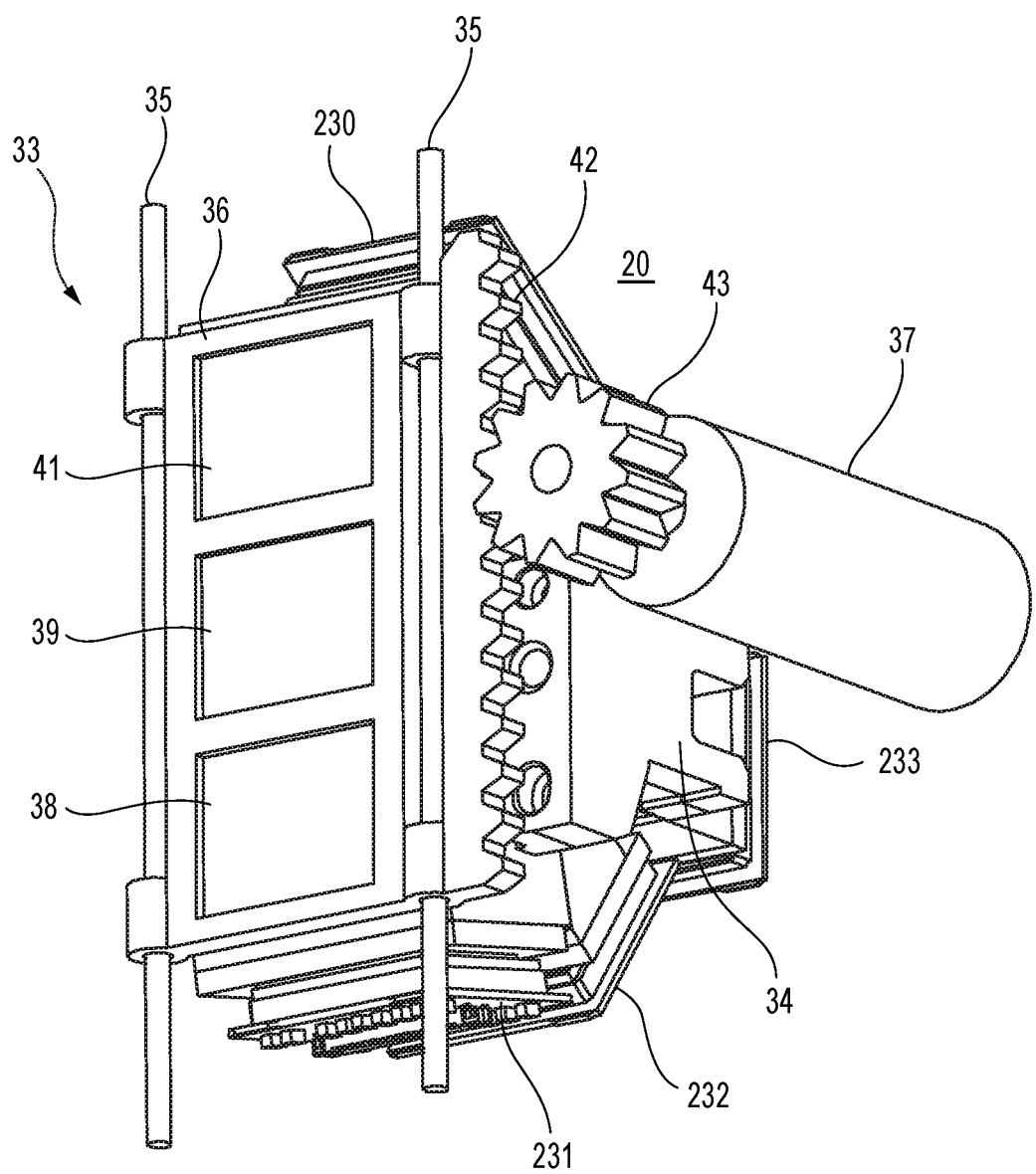
FIG. 9 is a perspective view of the filter unit provided on an objective side of the four-color separation prism.

FIG. 9 is a perspective view of the filter unit 33 provided on the objective side of the four-color separation prism 20. When any optical wavelength filter (the 5-ALA excitation-light cut filter 39 in an example in the figure) is moved by the drive motor 37, the optical wavelength filter is disposed to be opposite to the opening 32. In the four-color separation prism 20, the incident surface 220a of the IR separation prism 220 is disposed on an opposite side to the opening 32 with the 5-ALA excitation-light cut filter 39 interposed therebetween. For example, in a case of the 5-ALA mode, the 5-ALA excitation-light cut filter 39 is disposed at the opening 32. In the 5-ALA mode, light that has passed through the opening 32 from the target lesion is transmitted through the 5-ALA excitation-light cut filter 39 and is incident to the incident surface 220a of the IR separation prism 220.

Figure 10:
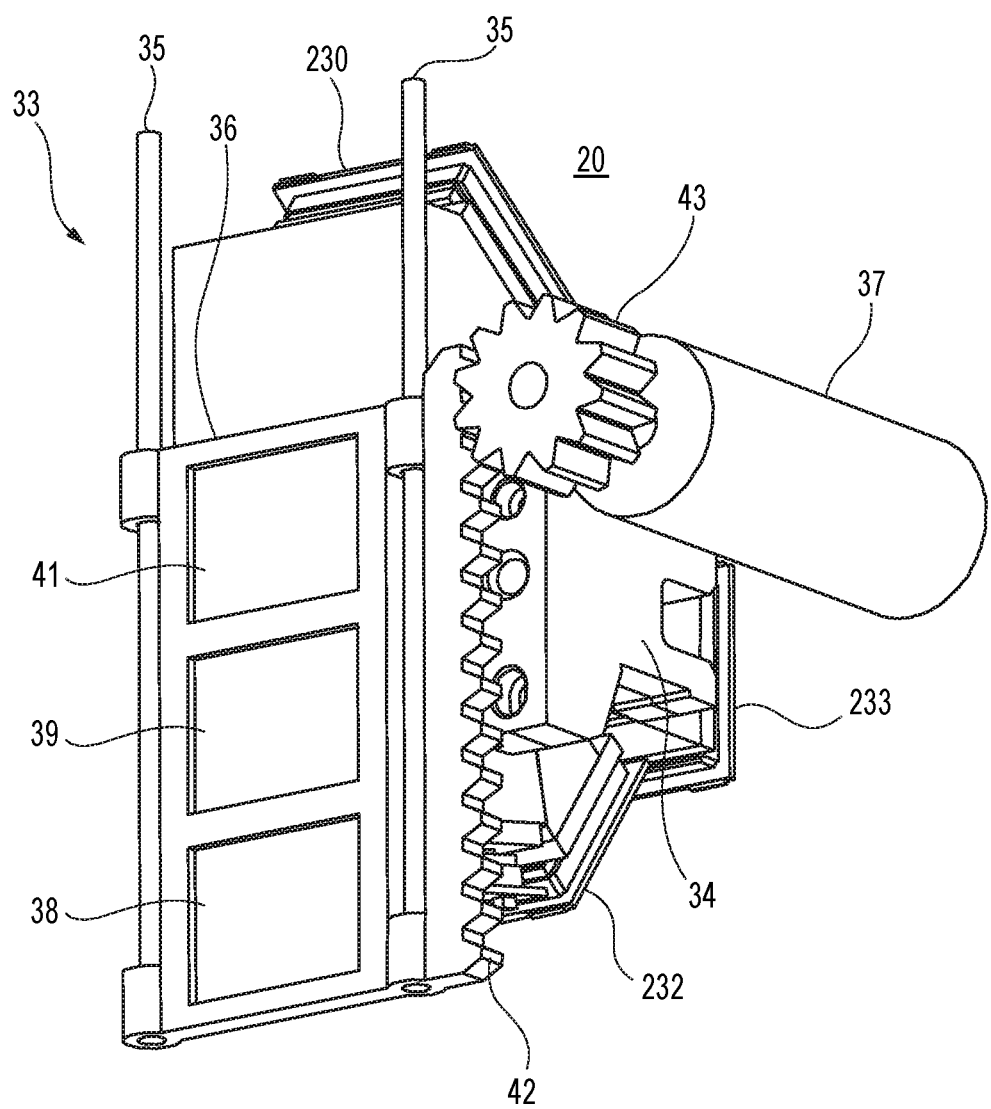
FIG. 10 is a perspective view of the filter unit when an ICG excitation-light cut filter is disposed at an opening.

FIG. 10 is a perspective view of the filter unit 33 when the ICG excitation-light cut filter 41 is disposed at the opening 32. When the ICG and visible light modes are designated by the operation (an example of a predetermined user operation) of the operation switch 44, the drive motor 37 is driven, a rotation direction and a rotation angle of the pinion 43 are controlled, and the ICG excitation-light cut filter 41 is disposed to be opposite to the opening 32. In the ICG and visible light modes, light that has passed through the opening 32 from the target lesion is transmitted through the ICG excitation-light cut filter 41 and is incident to the incident surface 220a of the IR separation prism 220.

Figure 11:
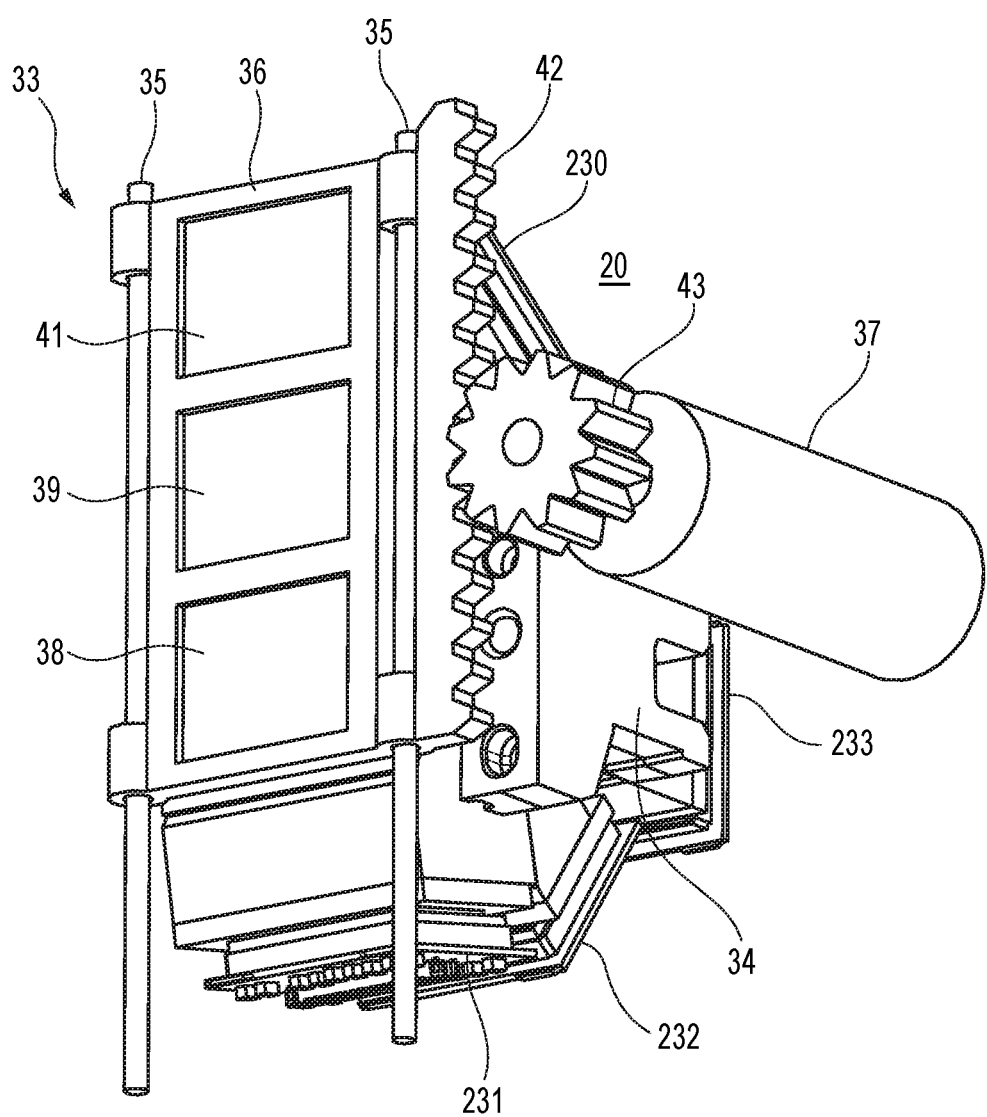
FIG. 11 is a perspective view of the filter unit at a time point in the middle of disposing an IR cut filter at the opening.

FIG. 11 is a perspective view of the filter unit 33 in the middle of disposing the IR cut filter 38 at the opening 32. When the visible light mode is designated by the operation (an example of the predetermined user operation) of the operation switch 44, the drive motor 37 is driven, the rotation direction and the rotation angle of the pinion 43 are controlled, and the IR cut filter 38 is disposed to be opposite to the opening 32. In the ICG and visible light modes, light that has passed through the opening 32 from the target lesion is transmitted through the IR cut filter 38 and is incident to the incident surface 220a of the IR separation prism 220.

Figure 12:
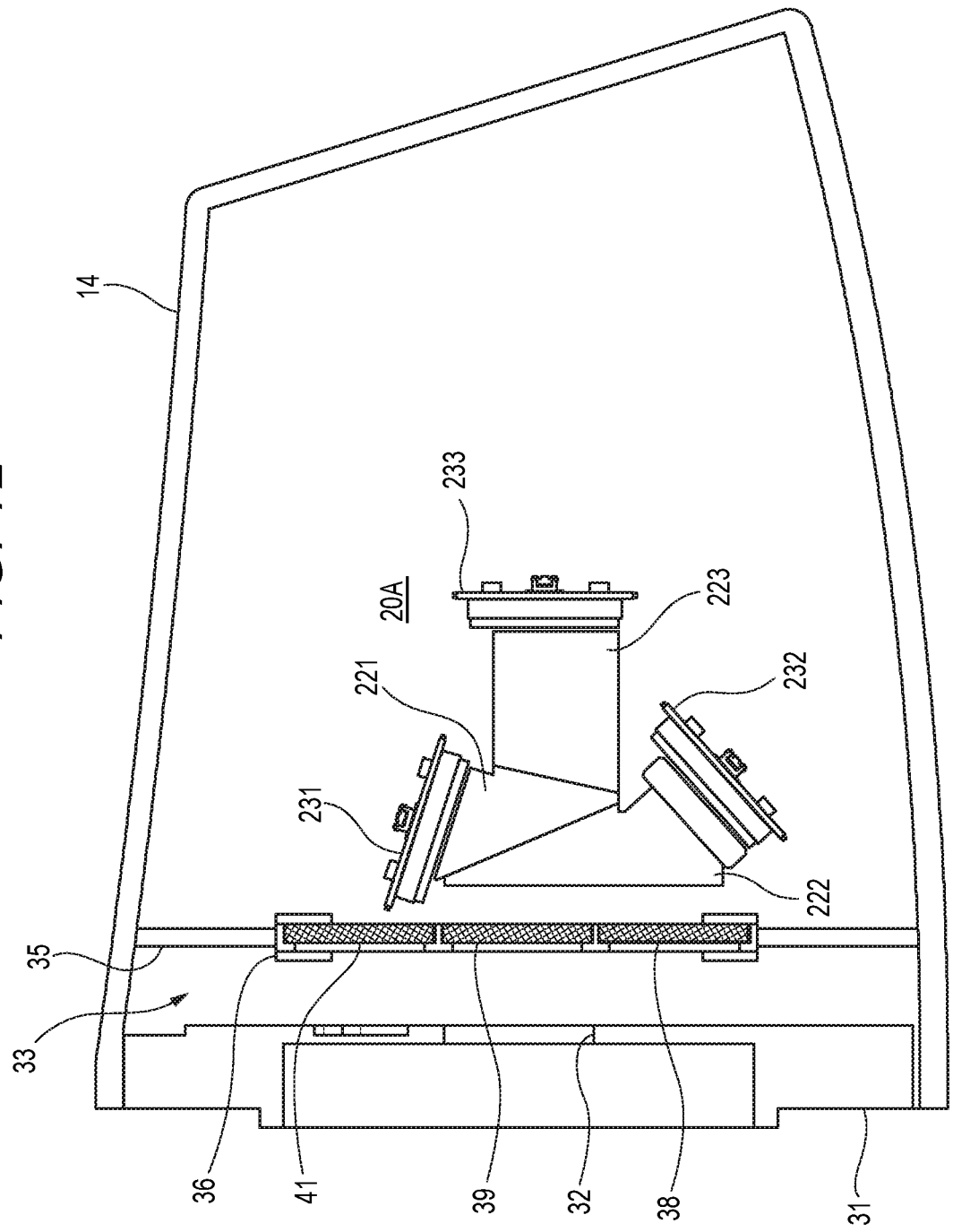
FIG. 12 is a side view of an example of a configuration in which the filter unit is provided to a three-color separation prism.

FIG. 12 is a side view of an example of a configuration in which the filter unit 33 is provided to a three-color separation prism 20A. The color separation prism that is used in the endoscope 10 according to the embodiment is not limited to the four-color separation prism 20. For example, the endoscope 10 may include a three-color separation prism 20A configured with a three-board type of B, G, and R. In FIG. 12, a configuration in which the image sensor 232 is provided in the red separation prism 222, the image sensor 231 is provided in the blue separation prism 221, and the image sensor 233 is provided in the green separation prism 223 is exemplified; however, the three-color separation prism 20A is not limited thereto. For example, the green separation prism, the blue separation prism, and the green separation prism are disposed in this order from the objective side; however, it is needless to say that the order of disposition is not limited thereto. Even in this case, similar to the configuration described above, it is possible to provide the filter unit 33 between the aperture member 31 and the three-color separation prism 20A.

In addition, in the embodiment, a configuration in which the plurality of optical wavelength filters are moved by the drive motor 37 driving the rack 42 and the pinion 43 is described; however, a moving mechanism of the optical wavelength filter is not limited thereto. Otherwise, it is possible to configure a mechanism that moves the optical wavelength filter by causing the optical wavelength filter to linearly slide by a linear motor using a permanent magnet and an electromagnet, for example. Further, it is possible to employ a mechanism that moves the optical wavelength filter by transmitting power that is manually generated in response to a switch operation by a user (for example, a doctor or an assistant for surgery or an examination, the same hereinafter) and causing the optical wavelength filter to linearly slide.

FIG. 13 is a block diagram showing an example of a configuration of an endoscope system 5 according to the embodiment. The endoscope system 5 is configured to include the endoscope 10, the CCU 30, and a display unit 40. The camera head 14 of the endoscope 10 includes the four-color separation prism 20 and the image sensors 230, 231, 232, and 233 described above. In FIG. 13, the camera head 14 further includes element driving units 141i, 141r, 141b, and 141g, a drive signal generating unit 142, a synchronizing signal generating unit 143, and a signal output unit 145.

The element driving unit 141i drives the image sensor 230 in response to a drive signal. The element driving unit 141r drives the image sensor 231 in response to a drive signal. The element driving unit 141b drives the image sensor 232 in response to a drive signal. The element driving unit 141g drives the image sensor 233 in response to a drive signal.

The drive signal generating unit 142 generates the drive signals for the element driving units 141i, 141r, 141b, and 141g. The synchronizing signal generating unit 143 corresponds to a function of a timing generator (TG) open circuit and supplies a synchronizing signal (timing signal) to the drive signal generating unit 142 and the like.

The signal output unit 145 transfers the electric signals from the image sensors 230, 231, 232, and 233 via a signal cable 14z to the CCU 30 in the LVDS method, for example. The signal output unit 145 may transmit the synchronizing signal from the synchronizing signal generating unit 143 to the CCU 30 via the signal cable 14z. The signal output unit 145 may transmit an operation signal from the operation switch 19 to the CCU 30 via the signal cable 14z. The signal output unit 145 corresponds to a function of a signal output circuit.

The operation switch 44 outputs operation signals input in response to the user operations to the drive motor 37 and the signal output unit 145. The signal output unit 145 may transmit the operation signal from the operation switch 44 to the CCU 30 via the signal cable 14z. Consequently, the CCU 30 is capable of specifically recognize which mode (for example, any one of the visible light mode, the 5-ALA mode, and the ICG mode) is currently operated.

The CCU 30 executes a program that is stored in an internal or external memory (not shown) of the CCU 30, thereby realizing various functions. The various functions include an RGB signal processor 22, an IR signal processor 23, and an output unit 28.

The RGB signal processor 22 converts the electric signals having the B component, the R component, and the G component from the image sensors 231, 232, and 233 into a video signal that can be displayed on the display unit 40 and outputs the video signal to the output unit 28.

The IR signal processor 23 converts the electric signal having the IR component from the image sensor 230 into a video signal and outputs the video signal to the output unit 28. In addition, the IR signal processor 23 may have a gain adjusting unit 23z. The gain adjusting unit 23z adjusts amplification (gain) when the electric signal having the IR component from the image sensor 230 for IR is converted into the video signal. For example, the gain adjusting unit 23z may adjust signal strength of the video signal having the RGB component and signal strength of the video signal having the IR component substantially to the same degree.

The gain adjusting unit 23z enables a user to reproduce an IR image having any strength with respect to the RGB image. Instead of or in addition to adjusting the amplification of the electric signal having the IR component, the RGB signal processor 22 may adjust amplification of the electric signal having the RGB component.

The RGB signal processor 22 and the IR signal processor 23 receives the synchronizing signal from the synchronizing signal generating unit 143 when performing signal processing and thus the processors operate in response to the synchronizing signal. Consequently, the image (video) having the RGB color components and the image having the IR component are adjusted such that a time deviation does not occur.

The output unit 28 outputs at least one of the video signal having the RGB components and the video signal having the IR component to the display unit 40 in response to the synchronizing signal from the synchronizing signal generating unit 143. The display unit 40 is set in a simultaneous output mode or a superimposed output mode, and the set mode is recognized by information (for example, a graph) representing which mode, which is stored in the CCU 30. For example, the output unit 28 recognizes which one of the simultaneous output mode or the superimposed output mode is currently set in the display unit 40 and outputs a video signal based on the simultaneous output mode or the superimposed output mode which is set.

Figure 14:
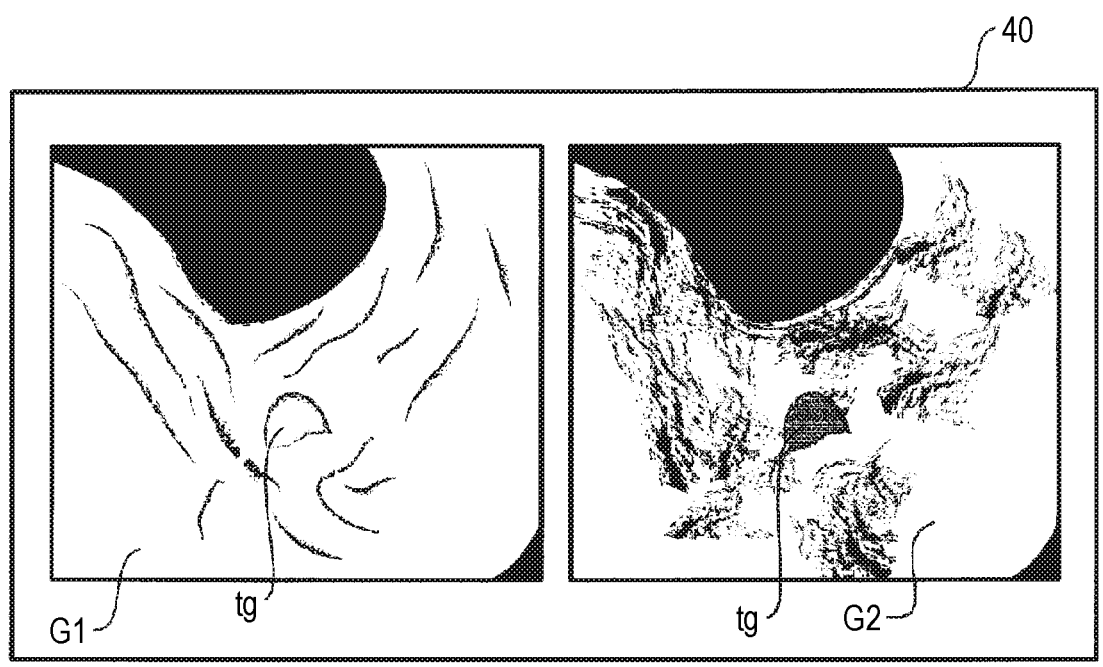
FIG. 14 is a schematic view showing an example of images during a simultaneous output mode.

In the simultaneous output mode, the output unit 28 simultaneously outputs an RGB image G1 and an IR image G2 (refer to FIG. 14) on separate screens. FIG. 14 is a schematic view showing an example of images during the simultaneous output mode. By the simultaneous output mode, it is possible to observe a target lesion tg by comparing the RGB image to the IR image on separate screens.

Figure 15:
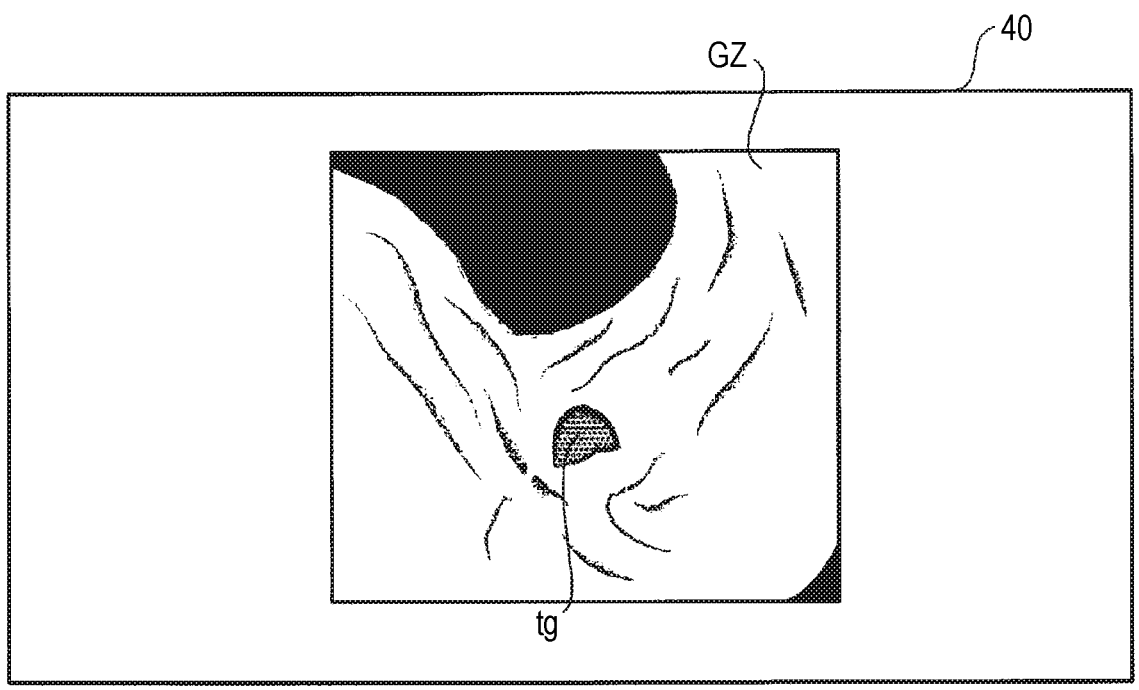
FIG. 15 is a schematic view showing an example of an image during a superimposed output mode.

In the superimposing output mode, the output unit 28 outputs a superimposed image GZ (refer to FIG. 15) in which the RGB image and the IR image are superimposed. FIG. 15 is a schematic view showing an example of an image during the superimposed output mode. For example, by the superimposing output mode, it is possible to clearly observe the target lesion tg having the fluorescence emission by the ICG and the IR light as illumination light in the RGB image.

A configuration in which the RGB signal processor 22, the IR signal processor 23, and the output unit 28 performs processing by software with a process in the CCU 30 cooperating with a memory therein is exemplified; however, a configuration in which the processing is performed by dedicated software may be employed.

The display unit 40 displays, on a screen, the image of an object such as the target lesion tg, which is imaged by the endoscope 10 and is output from the CCU 30, based on the video signal from the CCU 30. In the case of the simultaneous output mode, the display unit 40 divides the image into a plurality of (for example, two) images and displays by aligning the RGB image G1 and the IR image G2 on respective screens (refer to FIG. 14). In the superimposing output mode, the display unit 40 displays, on one screen, the superimposed image GZ in which the RGB image G1 and the IR image G2 are superimposed (refer to FIG. 15).

As described above, in the endoscope system 5, in a case where a site in a body is imaged by using the endoscope 10, indocyanine green (ICG) which is the fluorescent substance may be administered in the body the site (that is, the target lesion) such as an excessively accumulated tumor may be irradiated with near-infrared light such that the target lesion is illuminated, and the target lesion may be imaged.

The light L introduced to the light source connector 18 through the operation of the operation switch 19 by the user is guided to a distal side of the scope 11 and is projected from the imaging window 11z, and thereby a site around the target lesion, which includes the target lesion, is illuminated. Light reflected from the target lesion is guided to a rear side of the scope 11 through the imaging window 11z, converges on the relay lens 13, and is incident to the four-color separation prism 20 of the camera head 14.

In the four-color separation prism 20, of the incident light, the light having the IR component separated by the IR separation prism 220 is imaged as an optical image having the infrared light component by the image sensor 230 for IR. The light having the B component separated by the blue separation prism 221 is imaged as an optical image having the blue component by the image sensor 231 for blue. The light having the R component separated by the red separation prism 222 is imaged as an optical image having the red component by the image sensor 232 for red. The light having the G component separated by the green separation prism 223 is imaged as an optical image having the green component by the image sensor 233 for green.

The electric signal having the IR component converted by the image sensor 230 for IR is converted into the video signal by the IR signal processor 23 in the CCU 30 and is output to the output unit 28. The electric signals having the B component, the R component, and the G component converted by the image sensors 231, 232, and 233 for visible light are converted into the video signals by the RGB signal processor 22 in the CCU 30 and are output to the output unit 28. The video signals having the IR component and the video signals having the B component, the R component, and the G component are synchronized with each other and are output to the display unit 40.

In a case where the simultaneous output mode is set by the output unit 28, the display unit 40 displays the RGB image G1 and the IR image G2 simultaneously on two screens. The RGB image G1 is a color image obtained by irradiating the site including the target lesion tg with the visible light and imaging the target lesion. The IR image G2 is a black and white image (possible to set any color) obtained by irradiating the site including the target lesion tg with the IR light and imaging the target lesion.

In a case where the superimposing output mode is set by the output unit 28, the display unit 40 displays the superimposed image GZ in which the RGB image G1 and the IR image G2 are superimposed (synthesized).

According to the endoscope 10 of the embodiment, the image sensor 230 or IR receives the IR light, which is emitted from the IR separation prism 220 having the high transmittance of the IR light by using the four-color separation prism 20 in the endoscope 10. Therefore, the endoscope 10 is capable of increasing a receiving quantity of the IR light. Hence, there is no need to excessively amplify the signal having the IR component, and thus it is possible to suppress deterioration of the quality of the captured image by the endoscope 10, to which the IR component is added.

It is possible to more decrease the size of the image sensor by using the four-color separation prism 20 than the size of the image sensor of the single-board camera, and it is possible to miniaturize the endoscope 10. For example, the size of the image sensor of the single-board camera is 1 inch or 38 mm, and the image sensors 230 to 233 of the embodiment is ⅓ inch or larger.

In addition, in a mode in which the four-color separation prism 20 does not use the IR cut filter 38, the endoscope system 5 is capable of simultaneously outputting the RGB image and the IR image. Therefore, a user can check the entire site including the target lesion of the patient with the RGB image, for example, and can check the target lesion having the fluorescence emission with the IR image, and thus it is easy to visually recognize a position of the target lesion around the target lesion. Here, the RGB image is the image having the RGB component, and the IR image is the image having the IR component.

In addition, the image sensor 230 for IR, which converts the light having the IR component into the electric signal, may perform the adding process of the H/V pixel values and may output an electric signal having the added pixel values. Consequently the endoscope 10 is capable of more increasing the strength of the signal having the IR component, more highlighting the image having the IR component that is displayed by the display unit 40, and causing the target lesion to be easily recognized.

In addition, the endoscope system 5 may perform the gain adjustment such that the strength of the signals having the RGB components is substantially the same as the strength of the signal having the IR component. In this case, it is possible to equalize the pixel values of the RGB components and the pixel value of the IR component, and thus it is possible to easily view the image.

In addition, the endoscope system 5 may perform the gain adjustment such that there is a difference between the strength of the signals having the RGB components and the strength of the signal having the IR component. In this case, the endoscope system 5 is capable of displaying the RGB image and the IR image with a desired image quality by a user.

In addition, in a case of using the four-color separation prism 20, the strength of the signal having the IR component incident to the image sensor for IR is more increased, compared to a case of using the three-color separation prism. Therefore, the difference between the pixel values of the RGB component and the pixel value of the IR component decreases. Then, even when the electric signal, which is output from the image sensor 230 for IR, is excessively amplified by the CCU 30, it is possible to reproduce a color having a good balance between the RGB component and the IR component. Hence, while the amplification of the noise is suppressed, the endoscope system 5 obtains an image that clearly contains the RGB component and the IR component.

In addition, the RGB image and the IR image are simultaneously displayed on two screens. In this manner, the user can compare both of the images to each other, and thus user convenience improves.

In addition, the RGB image and the IR image are superimposed and displayed on one screen. In this manner, the user can compare the images of the RGB component and the IR component, and thus user convenience improves.

Figure 16:
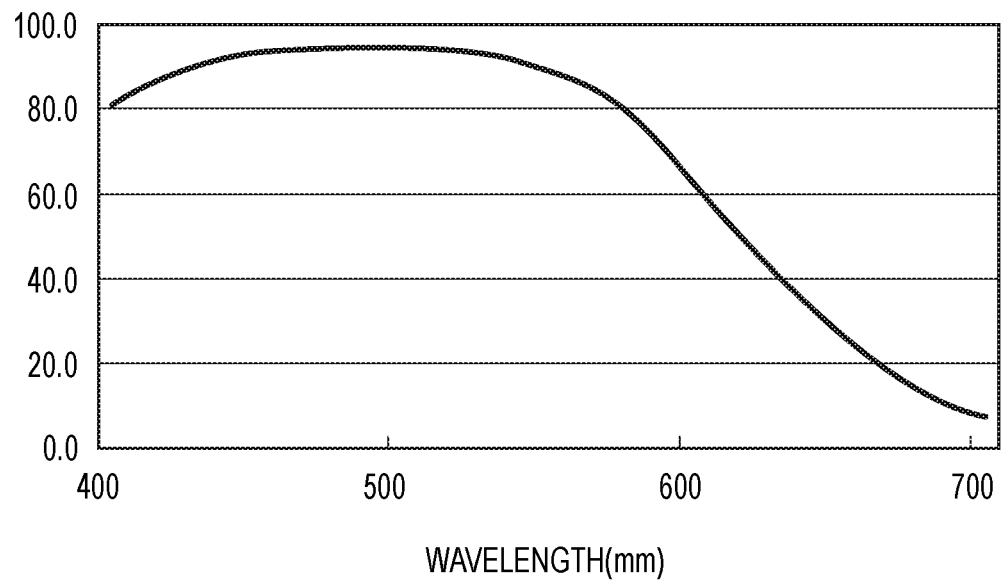
FIG. 16 is a graph showing an example of a spectral characteristic of the IR cut filter.

FIG. 16 is a graph showing an example of a spectral characteristic of the IR cut filter 38. The filter unit 33 includes the IR cut filter 38 as the IR cut filter, and thereby it is possible to cut the light having the IR component which is incident to the four-color separation prism 20.

Figure 17:
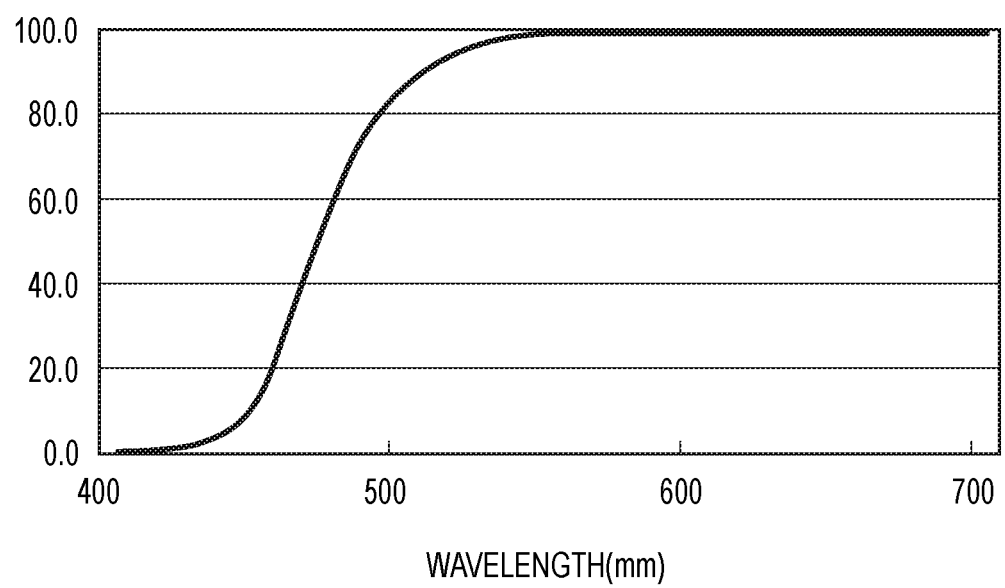
FIG. 17 is a graph showing an example of a spectral characteristic of a 5-ALA excitation-light cut filter.

FIG. 17 is a graph showing an example of a spectral characteristic of the 5-ALA excitation-light cut filter 39. The filter unit 33 includes the 5-ALA excitation-light cut filter 39, and thereby it is possible to cut, as the unnecessary light, the narrow-band excitation light (that is, the excitation light of 5-ALA which is the fluorescent substance) that includes a wavelength of 400 nm, which is incident to the four-color separation prism 20.

Figure 18:
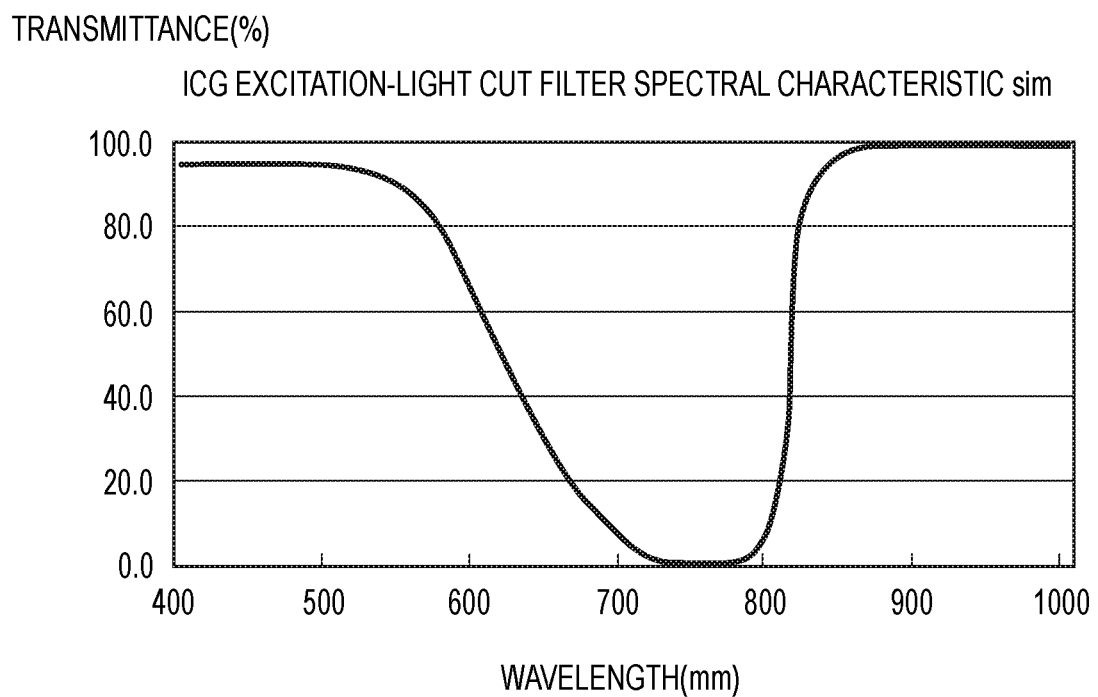
FIG. 18 is a graph showing an example of a spectral characteristic of the ICG excitation-light cut filter.

FIG. 18 is a graph showing an example of a spectral characteristic of the ICG excitation-light cut filter 41. The filter unit 33 includes the ICG excitation-light cut filter 41, and thereby it is possible to cut, as the unnecessary light, the narrow-band excitation light (that is, the excitation light of ICG which is the fluorescent substance) that includes a wavelength of 780 nm, which is incident to the four-color separation prism 20.

FIG. 19 is a graph showing an example of a total spectral characteristic without using the filter. In a case where various types of optical wavelength filters (the IR cut filter 38, the 5-ALA excitation-light cut filter 39, and the ICG excitation-light cut filter 41) included in the endoscope 10 according to the embodiment are used, the four-color separation prism 20 has the total spectral characteristic shown in FIG. 19. As described above, in FIG. 19, the vertical axis represents the transmittance, and the horizontal axis represents the wavelength. Hereinafter, the same is true of FIGS. 20, 21, and 22. In FIG. 19, h11 represents transmittance of light having the R component. h12 represents transmittance of light having the G component. h13 represents transmittance of light having the B component. h11 includes transmittance of light having the IR component.

Figure 20:
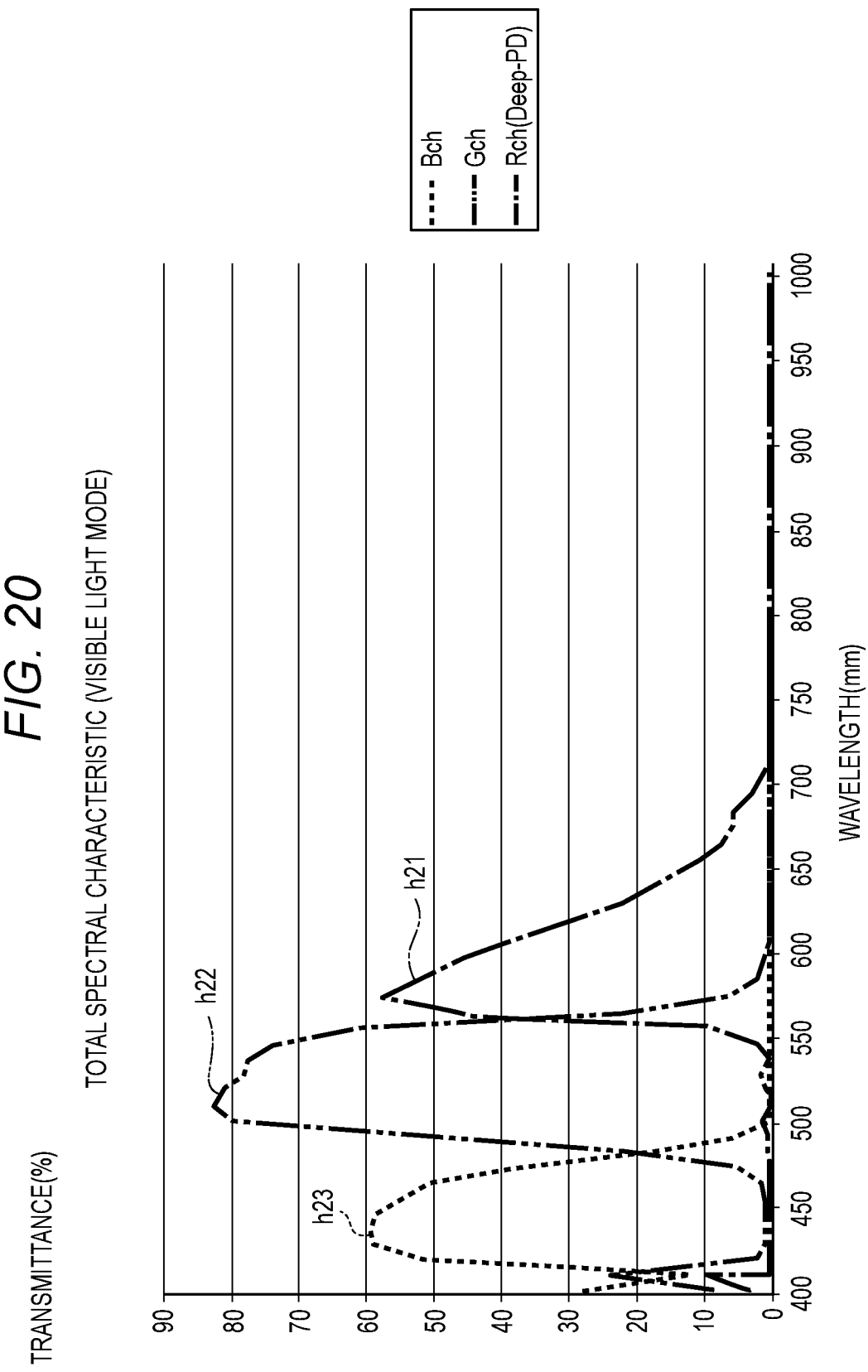
FIG. 20 is a graph showing an example of a visible light mode using the IR cut filter.

"Deep-PD" in FIGS. 19, 20, and 21 represents a deep-photo diode. The Deep-PD is a photoelectric conversion part in effective pixels of the image sensor. The Deep-PD means that a photo diode is deep. In the photo diode, when a light incident region is shallow, it is not possible to perform the photoelectric conversion in the near-infrared light having a long wavelength and the light is absorbed by a substrate. The Deep-PD is improved in the near-infrared sensitivity by having a deep light incident region of the photo diode. The Deep-PD is related to the ICG and visible light modes; however, the Deep-PD does not directly influence the visible light mode or the 5-ALA mode significantly.

For example, in a case of the three-color separation prism 20A of the three-board type, R is the Deep-PD, and thereby it is possible to simultaneously image not only red light (R light) but also the IR light having the wavelength approximate to that of the R light by one CH. Since the sensors are disposed to correspond to light beams in a case of the four-board type, there may be no particular reason to use the Deep-PD.

FIG. 20 is a graph showing an example of the visible light mode using the IR cut filter 38. In the visible light mode, the IR cut filter 38 is used, and thereby it is possible to cut the light having the IR component. In the total spectral characteristic, it is possible to more decrease transmittance h21 of the R component, compared to a case where the filter is not used as shown in FIG. 19. Transmittance h22 of the light having the G component and transmittance h23 of the light having the B component can be substantially the same as those obtained in a case where the filter is not used. As a result, the excitation light having the IR component is cut, and thereby it is possible to improve visibility of the image quality that has deteriorated due to mixing with the unnecessary light (the excitation light having the IR component or the like).

FIG. 21 is a graph showing an example of the 5-ALA mode using the 5-ALA excitation-light cut filter 39. The 5-ALA excitation-light cut filter 39 is used in the 5-ALA mode, thereby making it possible to cut the narrow-band 5-ALA excitation light including a wavelength of 400 nm. In the total spectral characteristic, it is possible to more decrease transmittance h33 of the light (narrow-band light having an approximate wavelength of 400 nm) having the B component, compared to the case where the filter is not used as shown in FIG. 19. Transmittance h32 of the light having the G component and transmittance h31 of the light having the R component can be substantially the same as those obtained in the case where the filter is not used. As a result, the 5-ALA excitation light is cut, and thereby it is possible to improve visibility of the image quality that has deteriorated due to mixing with the unnecessary light (particularly, the 5-ALA excitation light).

FIG. 22 is a graph showing an example of the visible light and ICG modes using the ICG excitation-light cut filter 41. The ICG excitation-light cut filter 41 is used in the ICG and visible light modes, thereby making it possible to cut the narrow-band ICG excitation light including a wavelength of 780 nm. In the total spectral characteristic, it is possible to more decrease transmittance h41 of a part of light (narrow-band light having an approximate wavelength of 780 nm) having the R component, compared to a case where the filter is not used as shown in FIG. 19. Transmittance h42 of the light having the G component and transmittance h43 of the light having the B component can be substantially the same as those obtained in a case where the filter is not used. As a result, the ICG excitation light is cut, and thereby it is possible to improve visibility of the image quality that has deteriorated due to mixing with the unnecessary light (particularly, the ICG excitation light).

As described above, in the endoscope 10 according to the embodiment, the light from the observation target site (for example, the target lesion) is incident to the opening 32, and the light that has passed through the opening 32 is transmitted selectively by using any one optical wavelength filter constituting the filter unit 33. In the endoscope 10, the color separation prism has the plurality of separation prisms and separates light, which has passed through the filter unit 33, into beams of light having different color components from each other in the four-color separation prism 20 having the plurality of separation prisms. The plurality of image sensors that are provided to correspond to the respective separation prisms perform the imaging based on the light having different color components separated by the respective separation prisms. In the endoscope 10, the signal output unit 145 outputs the image signals obtained by the imaging performed by the respective image sensors. In addition, in the endoscope 10, the drive motor 37 (an example of the filter disposing unit) disposes any one of the plurality of filters such that the light, which has passed through the opening 32, is able to be incident thereto.

Consequently, in the endoscope 10, the unnecessary light such as the excitation light for causing the fluorescence substance administered to the observation target site (for example, the target lesion in a human body) to have the fluorescence emission can be prevented from being reflected in the captured image in the ultrasonic diagnosis (for example, the fluorescence observation), and thus it is possible to achieve a captured image having a good image quality without performing the gain adjustment on the output of the signal having the target wavelength. As a result, an output of a signal having a target wavelength with low light intensity is amplified as in the technology in the related art, and thereby deterioration of the quality of the captured image, of which the S/N ratio has decreased, is solved. Therefore, it is possible to check the captured image of the observation target site (for example, the target lesion) in detail in the endoscopic diagnosis (for example, the fluorescence observation) by a user (for example, an observer such as a doctor).

In addition, the filter unit 33 is configured with the plurality of filters (specifically, the IR cut filter 38, the 5-ALA excitation-light cut filter 39, and the ICG excitation-light cut filter 41) which are substantially linearly aligned. The drive motor 37 causes the plurality of filters to substantially linearly slide in response to the predetermined user operation and disposes any one of the plurality of filters such that the light that has passed through the opening 32 can be incident to the filters. Consequently, in the endoscope 10, it is possible to switch any one of the plurality of filters by the predetermined user operation (for example, a simple operation such as pushing of the operation switch 44), and thus it is possible to perform multiple methods of surgery with one camera head without preparing respective dedicated camera heads. Further, since the filter unit 33 only moves in a substantially linear manner, the plurality of filters may only be disposed to be aligned in one dimensional direction, and thus it is possible to suppress an increase of the camera head 14 in size.

In addition, the plurality of filters constituting the filter unit 33 include the IR cut filter 38. Consequently, it is possible to cut the light having the IR component. As a result, the excitation light having the IR component is cut, and thereby it is possible to improve visibility of the image quality that has deteriorated due to mixing with the unnecessary light (the excitation light having the IR component or the like).

In addition, the plurality of filters constituting the filter unit 33 include the 5-ALA excitation-light cut filter 39. Consequently, the endoscope 10 is capable of cutting, during the imaging, the excitation light for causing the 5-ALA which is the fluorescence substance to have the fluorescence emission, the excitation light including the wavelength of 400 nm. As a result, the 5-ALA excitation light is cut, and thereby it is possible to improve visibility of the image quality that has deteriorated due to mixing with the unnecessary light (particularly, the 5-ALA excitation light).

In addition, the plurality of filters constituting the filter unit 33 include the ICG excitation-light cut filter 41. Consequently, the endoscope 10 is capable of cutting, during the imaging, the excitation light for causing the ICG which is the fluorescence substance to have the fluorescence emission, the excitation light including the wavelength of 780 nm. As a result, the ICG excitation light is cut, and thereby it is possible to improve visibility of the image quality that has deteriorated due to mixing with the unnecessary light (particularly. the ICG excitation light).

In addition, the plurality of separation prisms are disposed to have respective light flux centers Os of emitted light positioned along the same plane. The filters are orthogonal to the light flux center On of the incident light to the IR separation prism 220 disposed on the most objective side of the plurality of separation prisms and linearly move to be parallel to the same plane. Consequently, in the endoscope 10, it is possible to move the plurality of filters along the plane on which the separation prisms of the four-color separation prism 20 are arranged. Therefore, in the endoscope 10, a size of the camera head 14 in a width direction (direction perpendicular to the arranged plane) is not greatly changed. In other words, in the endoscope 10, it is possible to more miniaturize the camera head 14, compared to a turret type.

Further, the endoscope system 5 includes the endoscope 10 described above and the CCU 30 (an example of a controller) that generates the RGB image and the IR image based on the respective image signals output from the signal output unit 145 and displays the RGB image and the IR image on the display unit 40. Consequently, in the endoscope system 5, the unnecessary light such as the excitation light for causing the fluorescence substance administered to the observation target site (for example, the target lesion in a human body) to have the fluorescence emission can be prevented from being reflected in the captured image in the ultrasonic diagnosis (for example, the fluorescence observation), and thus it is possible to achieve a captured image having RGB and IR with a good image quality without performing the gain adjustment on the output of the signal having the target wavelength such that it is possible to display the captured image on the display unit 40. As a result, an output of a signal having a target wavelength with low light intensity is amplified as in the technology in the related art, and thereby deterioration of the quality of the captured image, of which the S/N ratio has decreased, is solved. Therefore, it is possible to check the captured image of the observation target site (for example, the target lesion) in detail in the endoscopic diagnosis (for example, the fluorescence observation) by a user (for example, an observer such as a doctor).

In addition, the endoscope system 5 further includes the operation switch 44 (an example of a switch) that transmits a filter switching signal for disposing any one of the plurality of filters such that the light, which has passed through the opening 32, is able to be incident to the filter or power, which is generated in response to a user operation (that is, a manual operation), to the drive motor 37 (an example of the filter disposing unit). Consequently, in the endoscope 10, it is possible to manually dispose a desired filter at the opening 32 and use the filter of the plurality of optical wavelength filters by the operation of the operation switch 44. As a result, in the endoscope 10, particularly, it is possible to realize high operability by the special light observation.

As described above, the embodiments are described with reference to the accompanying figures; however, it is needless to mention that the present disclosure is not limited to the examples. It is obvious for those skilled in the art to conceive various modification examples or alteration examples within the scope disclosed in the aspects of the present disclosure, and thus it is understood that the examples are included within the technical scope of this disclosure. In addition, the constituent elements may be optionally combined in the embodiments described above within a range without departing from the gist of the disclosure.

In the embodiment, a rigid endoscope is exemplified as the endoscope 10; however, the rigid endoscope which has another configuration or a flexible endoscope may be employed as long as the four-color separation prism 20 is used.

In the embodiment, a configuration in which the IR separation prism 220, the blue separation prism 221, the red separation prism 222, the green separation prism 223 are disposed in this order from a light incident side in the four-color separation prism 20 is exemplified; however, the order of disposition is only an example, and the prisms may be disposed in another order.

In the embodiment, the CCU 30 is described as an example of a processor. The processor may be configured physically in any different manner as long as the processor controls the endoscope system 5. Hence, the processor is not limited to the CCU 30. However, if the programmable CCU 30 is used, it is possible to change processing content by changing a program, and thus it is possible to increase flexibility of design of the processor. In addition, the processor may be configured with one semiconductor chip or may be configured of a plurality of semiconductor chips physically. In a case where the processor is configured with the plurality of semiconductor chips, types of control according to the embodiment described above may be realized by respective semiconductor chips. In this case, it is possible to consider that one processor is configured with the plurality of semiconductor chips. In addition, the processor may be configured with a member (capacitor or the like) having another function different from the semiconductor chip. In addition, the one semiconductor chip may be configured to realize a function of the processor and a function other than the function of the processor. In addition, if circuits installed in the electronic substrate 250 include a programmable circuit, it is possible to change processing content by changing a program. In addition, one or a plurality of circuits may be used.

The present application is based upon Japanese Patent Application (Patent Application No. 2017-174388) filed on Sep. 11, 2017, the contents of which are incorporated herein by reference.

What is claimed is:

1. An endoscope comprising:
an aperture portion having an opening to which light from an observation target site is incident;
a filter unit that has a plurality of filters aligned in a substantially straight line, and selectively transmits light, which has passed through the opening, based on any one of the filters;
a color separation prism that has a plurality of separation prisms which separate light, which has transmitted through the filter unit, into beams of light having different color components from each other;
a plurality of image sensors that are provided so as to respectively correspond to the separation prisms and capture an image based on the beams of light having different color components separated by the separation prisms respectively; and
a filter disposing unit that disposes any one of the plurality of filters so that the light, which has passed through the opening, is incident to the disposed one of the plurality of filters, wherein the filter disposing unit slides the plurality of filters along the substantially straight line in response to a predetermined user operation to dispose any one of the plurality of filters.

2. The endoscope according to claim 1,
wherein the plurality of filters include an IR cut filter.

3. The endoscope according to claim 1,
wherein the plurality of filters include a 5-ALA excitation-light cut filter.

4. The endoscope according to claim 1,
wherein the plurality of filters include an ICG excitation-light cut filter.

5. The endoscope according to claim 1,
wherein the plurality of separation prisms are disposed so that a light flux center of emitted light of each of the plurality of separation prisms is positioned along the same plane; and
wherein the filters are orthogonal to a light flux center of incident light of one of the separation prisms which is most close to the observation target site and linearly moves in a direction parallel to the same plane.

6. The endoscope according to claim 1,
wherein a shape of the plurality of filters corresponds to a shape of the aperture portion.

7. An endoscope system comprising:
an endoscope; and
a controller,
wherein the endoscope comprises:
an aperture portion having an opening to which light from an observation target site is incident;
a filter unit that has a plurality of filters aligned in a substantially straight line, and selectively transmits light, which has passed through the opening, based on any one of the filters;
a color separation prism that is formed by a plurality of separation prisms which separate light, which has transmitted through the filter unit, into beams of light having different color components from each other;
a plurality of image sensors that are provided so as to respectively correspond to the separation prisms and capture an image based on the beams of light having different color components separated by the separation prisms;
a filter disposing unit that disposes any one of the plurality of filters so that the light, which has passed through the opening is incident to the disposed one of the plurality of filters, wherein the filter disposing unit slides the plurality of filters along the substantially straight line in response to a predetermined user operation to dispose any one of the plurality of filters; and
wherein the controller generates and displays an RGB image and an IR image on a display unit.

8. The endoscope system according to claim 7, further comprising:
a switch that transmits a filter switching signal for disposing any one of the plurality of filters so that the light, which has passed through the opening, is incident to the disposed one of the plurality of filters or power in response to a user operation to the filter disposing unit.

9. The endoscope system according to claim 7,
wherein a shape of the plurality of filters corresponds to a shape of the aperture portion.

* * * * *